US009980895B2

(12) United States Patent
Ilekti et al.

(10) Patent No.: US 9,980,895 B2
(45) Date of Patent: May 29, 2018

(54) COSMETIC COMPOSITION FOR COATING KERATIN FIBRES

(71) Applicant: L'OREAL, Paris (FR)

(72) Inventors: Philippe Ilekti, Maisons-alfort (FR); Maitena Leuridan, Brie Comte Robert (FR); Chrystel Michallet-Geoffroy, Pringy (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 14/431,937

(22) PCT Filed: Oct. 11, 2013

(86) PCT No.: PCT/EP2013/071288
§ 371 (c)(1),
(2) Date: Mar. 27, 2015

(87) PCT Pub. No.: WO2014/060307
PCT Pub. Date: Apr. 24, 2014

(65) Prior Publication Data
US 2015/0250703 A1  Sep. 10, 2015

(30) Foreign Application Priority Data

Oct. 15, 2012 (FR) ..................... 12 59812

(51) Int. Cl.
| | |
|---|---|
| *A61K 8/81* | (2006.01) |
| *A61Q 1/10* | (2006.01) |
| *A61K 8/86* | (2006.01) |
| *A61K 8/92* | (2006.01) |
| *A61K 8/06* | (2006.01) |
| *A61Q 5/06* | (2006.01) |

(52) U.S. Cl.
CPC .............. *A61K 8/8135* (2013.01); *A61K 8/06* (2013.01); *A61K 8/8147* (2013.01); *A61K 8/8152* (2013.01); *A61K 8/86* (2013.01); *A61K 8/92* (2013.01); *A61K 8/922* (2013.01); *A61Q 1/10* (2013.01); *A61Q 5/06* (2013.01); *A61K 2800/43* (2013.01); *A61K 2800/59* (2013.01); *A61K 2800/87* (2013.01)

(58) Field of Classification Search
CPC .......... A61Q 1/10; A61K 8/8152; A61K 8/86; A61K 8/922
USPC ............................................. 424/70.7, 70.11
See application file for complete search history.

(56) References Cited

U.S. PATENT DOCUMENTS

| | | | |
|---|---|---|---|
| 5,849,278 A | 12/1998 | Piot et al. | |
| 5,858,338 A | 1/1999 | Piot et al. | |
| 6,517,823 B1 | 2/2003 | Norman et al. | |
| 2002/0156178 A1 | 10/2002 | Ascione et al. | |
| 2004/0198895 A1 | 10/2004 | Ascione et al. | |
| 2005/0118278 A1* | 6/2005 | Ananiev | A61K 8/19 424/617 |
| 2007/0246058 A1* | 10/2007 | Bodelin | A45D 40/265 132/218 |
| 2014/0328785 A1 | 6/2014 | Ilekti et al. | |
| 2014/0328786 A1 | 6/2014 | Ilekti et al. | |

FOREIGN PATENT DOCUMENTS

| | | |
|---|---|---|
| EP | 0 557 196 | 8/1993 |
| FR | 2 844 191 | 3/2004 |
| FR | 2 968 545 | 6/2012 |
| WO | 01 54660 | 8/2001 |
| WO | 02 065996 | 8/2002 |

OTHER PUBLICATIONS

Fiume et al, Title: Final report on the safety assessment of acrylates copolymer and 33 related cosmetic ingredients; International journal of toxicology, vol. 21, pp. 1-50, published 2002).*
Dow, title: Personal Care, ACULYN™ 22 Rheology Modifier/Stabilizer, published Sep. 2002. Downloaded from http://www.dow.com/assets/attachments/business/pcare/aculyn/aculyn_22/tds/aculyn22.pdf on Feb. 5, 2016.*
International Search Report dated Jun. 4, 2014 in PCT/EP13/071288 filed Oct. 11, 2013.
ALZO International Inc,"DERMOTHIX 100 Technical Bulletin", Internet Citation, XP002682321, Retrieved from the Internet : URL:http://www.classicdistrib.com/spec_sheets/Alzo_Dermothix-100.pdf ( 1 page), Aug. 24, 2012.
Li, C. et al., "Formation and properties of paraffin wax submicron emulsions prepared by the emulsion inversion point method", Colloids and Surfaces A: Physiochemical and Engineering Aspects, vol. 356, No. 1-3, pp. 71-77, XP026888196, 2010.

(Continued)

*Primary Examiner* — Yanzhi Zhang
(74) *Attorney, Agent, or Firm* — Oblon, McClelland, Maier & Neustadt, L.L.P.

(57) ABSTRACT

The present invention relates to an emulsion-type cosmetic composition for coating keratin fibers, comprising: —an aqueous phase, —particles comprising at least one hard wax, preferentially in the form of an aqueous dispersion, having a melting point greater than or equal to 60° C., the hard wax(es) being present at a total content greater than or equal to 10% by weight relative to the total weight of the composition, —at least one emulsifying system capable of dispersing at least the hard wax(es), comprising a non-ionic surfactant with an HLB value at 25° C. greater than or equal to 8, preferably greater than or equal to 10, and —at least one particular anionic associative polymer. The present invention also relates to a method for coating keratin fibers, to a method for preparing a cosmetic composition for coating keratin fibers, to a cosmetic composition for coating keratin fibers which is obtained by means of said production method, and also to a particular use.

20 Claims, No Drawings

(56) References Cited

OTHER PUBLICATIONS

"Long Curl Mascara", Database GNPD [Online], MINTEL; XP002700181, (1 page), Jun. 2008.
U.S. Appl. No. 14/433,761, filed Apr. 6, 2015, Ilekti, et al.
U.S. Appl. No. 14/432,369, filed Mar. 30, 2015, Ilekti.
U.S. Appl. No. 14/432,011, filed Mar. 27, 2015, Ilekti, et al.
U.S. Appl. No. 14/432,059, filed Mar. 27, 2015, Ilekti, et al.

* cited by examiner

COSMETIC COMPOSITION FOR COATING KERATIN FIBRES

The present invention relates to a cosmetic composition for coating keratin fibres, in particular the eyelashes or eyebrows. In particular, said cosmetic composition is a composition for making up and optionally caring for the eyelashes. The present invention also relates to a method for coating keratin fibres, in particular to a method for making up and optionally caring for the eyelashes. The present invention also relates to a method for producing a cosmetic composition for coating keratin fibres and also to a composition obtained by means of such a production method. The present invention also relates to particular uses.

The composition used can in particular be provided in the form of a product for the eyelashes, such as a mascara, or a product for the eyebrows. More preferentially, the invention relates to a mascara. The term "mascara" is understood to mean a composition intended to be applied to the eyelashes: it can be a composition for making up the eyelashes, a base for making up the eyelashes (also known as base coat), a composition to be applied over a mascara, also known as top coat, or a composition for the cosmetic treatment of the eyelashes. The mascara is more particularly intended for human eyelashes but also for false eyelashes.

Mascaras are prepared in particular according to two types of formulation: water-based mascaras, known as cream mascaras, in the form of a dispersion of waxes in water; anhydrous mascaras or mascaras with a low water content, known as waterproof mascaras, in the form of dispersions of waxes in organic solvents.

Generally, anhydrous mascaras have a good water resistance, but the level of volume is generally low and they are difficult to remove, whereas water-based mascaras have a lower water resistance but a high level of volume and are easier to remove.

The present application relates more specifically to "water-based" mascaras.

Compositions for coating keratin fibres with such a type of mascara generally consist of at least one fatty phase generally formed of one or more waxes dispersed in an aqueous liquid phase by means of an emulsifying system or conveyed in an organic solvent.

The application of mascara is aimed in particular at increasing the volume of the eyelashes and consequently at increasing the intensity of the gaze. Numerous thickening or volumizing mascaras exist to do this, the principle of which consists in depositing the maximum amount of material onto the eyelashes so as to obtain this volumizing (or charging) effect. It is in particular by means of the amount of particles (in particular waxes) that the desired application specificities for the compositions can be adjusted, such as, for example, their fluidity or consistency, and also their thickening power (also known as the charging or making-up power).

However, one problem encountered is that the conventional routes for formulating water-based mascaras do not make it possible to exceed a high solids content, for example greater than or equal to 42%, for fear of obtaining a texture which is too thick.

An aim of the present application is more particularly to provide a mascara in the form of an emulsion, preferably with a high solids content, for example greater than or equal to 42%.

More particularly, an aim of the present invention consists in stabilising a direct emulsion rich in fatty substances, in particular in waxes, without phase separation over time and/or caused by UV radiation and/or caused by light.

An aim of the present application is more particularly to provide a stable mascara exhibiting a texture which is sufficiently thick to obtain a charging deposited layer, of satisfactory consistency, enabling easy application to the eyelashes and an even deposited layer, that is to say a layer which is smooth and homogeneous, even after being stored at 4° C. for two months.

Another aim of the present application is to provide a stable mascara exhibiting a texture which is sufficiently thick to obtain a charging deposited layer, of satisfactory consistency, enabling easy application to the eyelashes and an even deposited layer, that is to say a layer which is smooth and homogeneous, even after being stored at 45° C. for two months.

An aim of the present application is more particularly to provide a stable mascara exhibiting a texture which is sufficiently thick to obtain a charging deposited layer, of satisfactory consistency, enabling easy application to the eyelashes and an even deposited layer, that is to say a layer which is smooth and homogeneous, even after being stored for two months at temperatures oscillating between 4° C. and 45° C.

An aim of the present application is more particularly to provide a mascara in which the waxes are homogeneously dispersed.

An aim of the present application is more particularly to provide a mascara in which the pigments are homogeneously dispersed.

An aim of the present application is more particularly to provide a mascara which is pleasant to apply.

An aim of the present invention is more particularly to provide a composition for coating keratin fibres which makes possible good separation of the eyelashes during its application, without formation of bunches of eyelashes, and while ensuring smooth and even deposition of material (without lumps of composition).

An aim of the present invention is more particularly to obtain a composition for coating keratin fibres, preferably a mascara, which has good application properties in terms of slip and of playtime (redeposition, retouching).

Another aim of the present invention is to obtain a composition for coating keratin fibres, preferably a mascara, which gives rise to a volume effect on the eyelashes.

Another aim of the present invention is to obtain a composition for coating keratin fibres, preferably a mascara, which has a good wear property on the eyelashes.

Another aim of the present invention is to obtain a composition for coating keratin fibres, preferably a mascara, which gives rise to a charging or covering deposited layer.

Another aim of the present invention is to obtain a composition for coating keratin fibres, preferably a mascara, which has good lengthening properties for the eyelashes coated with such a composition.

Another aim of the present invention is to obtain a composition for coating keratin fibres, preferably a mascara, which has good curling properties for the eyelashes coated with such a composition.

Another aim of the present invention is to obtain a composition for coating keratin fibres, preferably a mascara, which has good black intensity, from a colorimetry and chromaticity point of view.

Another aim of the present invention is to obtain a composition for coating keratin fibres, preferably a mascara, which has good adhesion to the eyelashes.

In particular, an aim of the present invention is to prepare a composition for coating keratin fibres which has a good wear property, and is resistant to rubbing and/or to water, and in particular to ambient moisture, tears, sweat and/or sebum, while at the same time being easy to remove.

Consequently, a subject of the present invention is a cosmetic composition for coating keratin fibres, preferably the eyelashes, preferably a mascara composition, of the emulsion type, preferably wax(es)-in-water emulsion type, comprising:
  an aqueous phase,
  particles comprising at least one hard wax, preferentially present in the form of at least one aqueous dispersion of particles of hard wax(es) having a melting point greater than or equal to 60° C., the hard wax(es) being present at a total content greater than or equal to 10% by weight, relative to the total weight of the composition,
  at least one emulsifying system capable of dispersing at least the hard wax(es), preferably comprising at least one non-ionic surfactant with an HLB value at 25° C. greater than or equal to 8, preferably greater than or equal to 10,
  at least one anionic associative polymer comprising:
    i) a backbone chain derived from at least one monomer comprising at least one carboxylic acid and at least one α,β-monoethylenic unsaturation, an ester or esters thereof, a salt or salts thereof, and a mixture thereof,
    ii) at least one hydrophobic chain extending laterally relative to said backbone chain, and
    iii) at least one alkoxylated or glycerolated spacer linking said backbone chain and said hydrophobic chain(s).

According to one preferred embodiment, the particles in accordance with the invention comprise:
  * at least one hard wax, preferentially present in the form of at least one aqueous dispersion of particles of hard wax(es) having a melting point greater than or equal to 60° C., the hard wax(es) being present at a total content greater than or equal to 10% by weight relative to the total weight of the composition, and
  * preferably at least one aqueous dispersion of particles of at least one film-forming polymer, the film-forming polymer(s) preferably being present at a dry matter content greater than or equal to 5%, preferably greater than or equal to 10% by weight relative to the total weight of said composition.

Surprisingly and unexpectedly, the inventors of the present application have solved this or these problem(s) by means of such a composition. In particular, a composition in accordance with the invention gives rise to a composition in the form of an emulsion, which can be rich in solids, in particular in fatty substances, which is stable, and which has a homogeneous and even dispersion of waxes, even after 2 months, whether at 45° C. or at 4° C. It appears that such a composition also exhibits a good dispersion of the pigments, is smooth and glossy and exhibits an intense black. Such a composition is also pleasant to apply and comfortable, and exhibits a volume effect. Furthermore, this composition exhibits good water resistance by virtue of a large presence of film-forming particles as an aqueous dispersion, without having a great impact on the volume effect.

According to a second aspect, another subject of the present invention is an assembly or kit for coating keratin fibres, comprising:
  at least one cosmetic composition for coating keratin fibres as described above, and
  at least one applicator for the composition, said applicator comprising means, where appropriate as protruding elements, configured in order to engage with said keratin fibres, such as the eyelashes or eyebrows, so as to smooth and/or separate the eyelashes or eyebrows. Such protruding elements can comprise teeth, bristles or the like. Said assembly, in particular said applicator, can optionally be equipped with means for vibrating and/or heating said composition.

According to a third aspect, another subject of the present invention is an assembly or kit for packaging and applying a composition for coating keratin fibres, comprising:
  a device for packaging said cosmetic composition for coating keratin fibres as described above,
  an applicator for said composition.

Said applicator can be rigidly connected to a grasping member forming a cap for said packaging device. In other words, said applicator may be mounted in a removable position on said device between a closed position and an open position of a dispensing aperture of the device for packaging said composition.

According to a fourth aspect, another subject of the present invention is a method for coating keratin fibres, in particular for making up the eyelashes, comprising a step of application of a cosmetic composition for coating keratin fibres as described above.

According to a fifth aspect, another subject of the present invention is a method for preparing, or producing, a composition as defined above, consisting of the steps of:
  in a first phase, heating the hard wax(es) and optionally the additional wax(es) at a temperature above its (their) melting point in order to melt the wax(es), adding the anionic associative polymer(s) as described above, adding at least one emulsifying system capable of dispersing at least the hard wax(es), preferably comprising at least one non-ionic surfactant with an HLB value at 25° C. greater than or equal to 8, preferably greater than or equal to 10, adding water, it being given that the water content used is greater than 25% by weight relative to the total weight of this first phase, preferably greater than 30% by weight, or even greater than 35% by weight, relative to the total weight of this first phase, and that the total content of hard wax(es), and optionally of additional wax(es), and the total content of emulsifying system(s) are such that the weight ratio of the hard wax(es) plus additional wax(es)/emulsifying system(s) (the emulsifying system to be considered for this calculation preferably being the non-ionic surfactant(s) with an HLB at 25° C. greater than or equal to 8, preferably greater than or equal to 10), is inclusively between 2 and 6, more preferentially between 3 and 5, adding the colorants, optionally adding any other compound of thickening nature, such as gums, fillers, pasty fatty substances, or water-soluble film-forming polymers, the order of addition being of no importance, it being understood, however, that it is preferable for the water not to be present at first in order to avoid any early evaporation, emulsifying the whole mixture with stirring at a temperature above the melting point of the wax(es),
  in a second phase, placing an aqueous phase optionally comprising, or optionally being formed by, an aqueous dispersion of particles of film-forming polymers in a vessel in which the temperature, which is preferably regulated, is inclusively between 0 and 45° C. and preferably between 0 and 20° C., the order in which the first phase and the second phase are prepared being of no importance,
  bringing the first and second phases together by pouring the first phase, still at a temperature above the melting point of the wax(es), into the vessel containing the second phase having a temperature, which is preferably regulated, between 0 and 45° C. and preferably between 0 and 20° C., leaving to stir until the temperature of the mixture stabilizes at the temperature, which is preferably regulated, between 0 and 45° C. and preferably between 0 and 20° C., preferentially adding a preserving system, preferably once the temperature of the mixture of the first phase with the second phase has stabilized at the temperature, which is preferably regulated, inclusively between 0 and 45° C. and preferably between 0 and 20° C., preferentially adding a base, such as KOH, able to neutralize the anionic associative polymer(s).

According to a sixth aspect, another subject of the present invention is a composition obtained by means of said method of production as described above.

According to a seventh aspect, another subject of the present invention is the use of a method of preparation as described above, for obtaining makeup compositions, in particular mascara compositions, which are preferentially black, smooth, glossy and/or, preferably, of intense colour.

Throughout the description which follows and unless expressly mentioned:

- the term "alkyl" means a saturated, linear or branched, $C_8$-$C_{24}$, better still $C_{12}$-$C_{20}$ and more preferentially $C_{14}$-$C_{18}$, hydrocarbon-based chain.
- The term "acyl" means a saturated, linear or branched, $C_8$-$C_{24}$, better still $C_{12}$-$C_{20}$ and more preferentially $C_{14}$-$C_{18}$, hydrocarbon-based chain comprising a carboxyl function, the hydroxyl function (—OH) of which has been replaced.
- The term "additional wax(es)" is understood to mean any wax other than a hard wax, and thus soft wax(es).

According to particular preferred embodiments of the present invention concerning both the compositions and the methods described above and aimed at solving at least one of the above-mentioned problems:

- the emulsion is of the wax(es)-in-water type;
- the aqueous phase represents from 30% to 80% by weight and preferably from 40% to 70% by weight, relative to the total weight of the composition;
- said composition comprises a fatty phase dispersed in the aqueous phase, the fatty phase comprising predominantly particles of hard wax(es), preferentially present in the form of an aqueous dispersion or aqueous dispersions;
- the total content of hard wax(es) and optionally of additional wax(es) and the total content of emulsifying system(s) are such that the weight ratio of the hard wax(es)+additional wax(es)/emulsifying system(s) is inclusively between 2 and 6, more preferentially between 3 and 5 (the emulsifying system to be considered for this calculation preferably being the non-ionic surfactant(s) with an HLB value at 25° C. greater than or equal to 8, preferably greater than or equal to 10);
- said composition is devoid of oil or organic solvent;
- the fatty phase represents 15% to 30% by weight, relative to the total weight of the composition;
- said composition comprises a solids content greater than or equal to 42%, preferentially greater than or equal to 45%, more preferentially greater than or equal to 48%, or even greater than or equal to 50%;
- the particles of hard waxes have, in said (final) composition, an average size expressed as volume-average "effective" diameter D[4,3] of less than or equal to 5 µm, preferentially less than or equal to 2 µm, even more preferentially less than or equal to 1 µm, for example between 0.01 and 5 µm and more preferentially between 0.05 and 2 µm;
- the particles of film-forming polymers introduced in the form of an aqueous dispersion or aqueous dispersions into said composition have, in said composition, an average size expressed as volume-average "effective" diameter D[4,3] of less than or equal to 5 µm, preferentially less than or equal to 2 µm, even more preferentially less than or equal to 1 µm, for example between 0.01 and 5 µm and more preferentially between 0.5 and 2 µm;
- said composition comprises a total content of particles of hard wax(es), preferentially present in the form of an aqueous dispersion, greater than or equal to 10% by weight, preferably greater than or equal to 15% by weight, relative to the total weight of the composition;
- said composition comprises a total content of particles of hard wax(es), preferentially present in the form of an aqueous dispersion or aqueous dispersions, representing at least 80% by weight, preferentially at least 90% by weight and more preferentially 100% by weight, relative to the total weight of wax(es);
- the total content of particles of hard wax(es), preferentially present in the form of an aqueous dispersion or aqueous dispersions, is greater than or equal to 30% by weight and preferentially greater than or equal to 40% by weight, relative to the total weight of the particles;
- the total content of particles of hard wax(es), preferentially present in the form of an aqueous dispersion or aqueous dispersions, represents at least 80% relative to the total weight of fatty substances;
- the hard wax(es) in the form of particles, preferentially present in the form of an aqueous dispersion or aqueous dispersions, is (are) polar;
- the anionic associative polymer(s) is (are) chosen from copolymers derived from (meth)acrylic acid/$C_1$-$C_8$, better still $C_1$-$C_3$, preferably $C_2$, alkyl (meth)acrylate/$C_8$-$C_{24}$, better still $C_{12}$-$C_{22}$, preferably $C_{16}$-$C_{22}$, even more preferentially $C_{18}$ or $C_{22}$, fatty alcohol (meth)acrylate, and a mixture thereof, which is alkoxylated or glycerolated;
- the anionic associative polymer(s) is (are) chosen from the copolymers having the following INCI names: Acrylates/Steareth-20 Methacrylate Copolymer, Acrylates/Beheneth-25 Methacrylate Copolymer, and a mixture thereof;
- the total content of anionic associative polymer(s) is greater than or equal to 0.05% by weight, better still greater than or equal to 0.1% by weight, relative to the total weight of the composition, preferably inclusively between 0.1% and 1% by weight, more preferentially between 0.2% and 0.8% by weight relative to the total weight of the composition;
- the hard wax(es) is (are) not introduced, in the production of a cosmetic composition according to the invention, preferentially of a mascara, in the form of an aqueous dispersion of preprepared particles;
- the particles of film-forming polymer(s) are introduced in the preparation of the composition in the form of a preprepared aqueous dispersion of film-forming polymer(s).

Indeed, the dispersion of the hard wax(es) is carried out in situ, using the hard wax(es) in the form of powder, or fatty substances, by forming an emulsion in a first preparation phase and by bringing together, in a second phase, the hard wax(es) emulsified with an aqueous dispersion of film-forming polymer(s) such that the water resulting from the aqueous dispersion of film-forming polymer(s) provides an aqueous dispersion of particles of hard wax(es);

said composition comprises a total content of particles of film-forming polymer(s), present in the form of an aqueous dispersion or aqueous dispersions, greater than or equal to 10% by weight, preferably greater than or equal to 15% by weight, relative to the total weight of the composition;

contrary to the hard wax(es), the film-forming polymer(s) in accordance with the invention is (are), during the production of a cosmetic composition according to the invention, preferentially of a mascara, introduced in the form of an aqueous dispersion of particles of film-forming polymer(s) which are predispersed, which advantageously has a specific emulsifying system, which is varied according to the chemistry of the film-forming polymer(s) used;

the particles of film-forming polymer(s) have a specific emulsifying system, i.e. a system which is distinct from the emulsifying system in accordance with the present invention, more particularly distinct from the non-ionic surfactant(s) with an HLB value at 25° C. greater than or equal to 8 or preferably greater than or equal to 10, which is (are) suitable for dispersing the hard wax(es);

the particles of hard wax(es) and the particles of film-forming polymers as an aqueous dispersion have a respective emulsifying system, more precisely a respective surfactant;

the total content of particles of film-forming polymer(s), present in the form of an aqueous dispersion or aqueous dispersions, is greater than or equal to 30% by weight and preferentially greater than or equal to 40% by weight, relative to the total weight of the solid particles;

the particles of film-forming polymer(s) present in the form of an aqueous dispersion or aqueous dispersions are chosen from synthetic polymers, of radical type or of polycondensate type, polymers of natural origin, and mixtures thereof;

the particles of film-forming polymer(s) present in the form of an aqueous dispersion or aqueous dispersions are chosen from dispersions of acrylic polymers, dispersions of polyurethane, dispersions of sulfopolyesters, vinyl dispersions, dispersions of polyvinyl acetate, dispersions of vinylpyrrolidone/dimethylaminopropylmethacrylamide/lauryldimethylpropylmethacrylamidoammonium chloride terpolymer, dispersions of polyurethane/polyacrylic hybrid polymers, dispersions of particles of core-shell type, and mixtures thereof, preferably from dispersions of acrylic polymers, dispersions of polyurethane/polyacrylic hybrid polymers, and derivatives thereof, and one or more mixture(s) thereof, preferentially from dispersions of acrylic polymers, in particular styrene-acrylic polymers, and dispersions of polyurethanes, in particular polyester polyurethanes, and derivatives thereof, and one or more mixture(s) thereof;

the total content of particles of hard wax(es) and the total content of particles of film-forming polymer(s), preferentially both present in the form of an aqueous dispersion or aqueous dispersions, are such that the weight ratio of the particles of hard wax(es) to the particles of film-forming polymer(s) is greater than or equal to 1/2, preferably greater than 2/3, advantageously between 1/2 and 2 and preferably between 2/3 and 3/2;

the non-ionic surfactant(s) with an HLB value at 25° C. greater than or equal to 8, preferably greater than or equal to 10, is (are) chosen from:

glycerol ethers which are preferably oxyalkylenated, oxyalkylenated alcohols,
fatty acid esters of polyethylene glycol,
esters of fatty acids and of glycerol ethers which are preferably oxyalkylenated,
esters of fatty acids and of sorbitol ethers which are preferably oxyalkylenated,
and mixture(s) thereof;
preferably, from esters of fatty acids and of glycerol ethers which are preferably oxyalkylenated;

the non-ionic surfactant(s) with an HLB value at 25° C. greater than or equal to 8, preferably greater than or equal to 10, is (are) present at a content greater than or equal to 3% by weight, relative to the total weight of the composition, preferably between 4% and 10% by weight relative to the total weight of the composition;

said composition comprises at least one or more additional surfactant(s), preferably one or more non-ionic surfactant(s) having, at 25° C., within the Griffin meaning, an HLB balance of less than 8; in such a case, the non-ionic surfactant(s) with an HLB value at 25° C. greater than or equal to 8, preferably greater than or equal to 10, is (are) preferably the major emulsifying system;

said composition comprises at least one water-soluble, film-forming polymer, more preferentially said composition is devoid of water-soluble, film-forming polymer;

said composition comprises at least one colorant chosen from one or more pulverulent colorant(s), preferably metal oxides and in particular iron oxides;

the metal oxide(s) is (are) preferably present at a content greater than or equal to 2% by weight relative to the total weight of the composition, and advantageously inclusively between 3% and 22% by weight relative to the total weight of the composition;

said composition comprises at least one hydrophilic and/or lipophilic gelling agent, preferably at least one hydrophilic gelling agent;

said composition has a viscosity at 25° C. ranging from 5 to 50 Pa·s, in particular measured using a Rheomat RM100® instrument;

said composition may be a makeup composition, a makeup base or base coat, or a "top coat" composition to be applied onto makeup;

Other characteristics, properties and advantages of the present invention will emerge more clearly on reading the description and the examples that follow.

Aqueous Phase

The composition according to the invention comprises an aqueous phase, which can form a continuous phase of the composition.

The aqueous phase comprises water. It can also comprise at least one water-soluble solvent.

In the present invention, the term "water-soluble solvent" denotes a compound which is liquid at ambient temperature and which is miscible with water. The water-soluble solvents which can be used in the compositions according to the invention can in addition be volatile.

Mention may in particular be made, among the water-soluble solvents which can be used in the compositions in accordance with the invention, of lower monoalcohols having from 1 to 5 carbon atoms, such as ethanol and isopropanol, and glycols having from 2 to 8 carbon atoms, such as ethylene glycol, propylene glycol, 1,3-butylene glycol and dipropylene glycol.

The aqueous phase (water and optionally the water-miscible solvent) is generally present in the composition according to the present application at a content ranging from 30% to 80% by weight, relative to the total weight of the composition, preferably ranging from 40% to 70% by weight relative to the total weight of the composition. This aqueous phase content includes not only the water originating from the aqueous dispersions of film-forming polymers and, where appropriate, from the aqueous dispersions of hard waxes, in accordance with the invention, but also, where appropriate, the water intentionally added to the composition.

Solids Content

The composition according to the invention advantageously comprises a solids content greater than or equal to 42%, in particular greater than or equal to 45%, or even greater than or equal to 48%, and preferentially greater than or equal to 50%.

Within the meaning of the present invention, the "solids content" denotes the content of non-volatile matter.

The solids content (abbreviated to SC) of a composition according to the invention is measured using a "Halogen Moisture Analyzer HR 73" commercial halogen drying device from Mettler Toledo. The measurement is carried out on the basis of the weight loss of a sample dried by halogen heating and thus represents the percentage of residual matter once the water and the volatile matter have evaporated.

This technique is fully described in the documentation of the device supplied by Mettler Toledo.

The measurement protocol is as follows:

Approximately 2 g of the composition, hereinafter the sample, are spread out over a metal dish, which is introduced into the abovementioned halogen drying device. The sample is then subjected to a temperature of 105° C. until an unchanging weight is obtained. The wet weight of the sample, corresponding to its initial weight, and the dry weight of the sample, corresponding to its weight after halogen heating, are measured using a precision balance.

The experimental error associated with the measurement is of the order of plus or minus 2%.

The solids content is calculated in the following way:

Solids content (expressed as % by weight)=100×(dry weight/wet weight).

A composition according to the invention comprises particles of waxes, particles of film-forming polymer(s), and at least one particular emulsifying system.

Emulsifying System

A composition according to the invention comprises an emulsifying system.

This emulsifying system is capable of dispersing the particles of hard wax(es) and optionally the additional wax(es). It may also be capable of dispersing the particles of film-forming polymer(s); however, the particles of film-forming polymer(s) can have a specific emulsifying system, distinct from that capable of dispersing the particles of hard wax(es) and optionally the additional wax(es).

More specifically, a composition according to the invention comprises at least one non-ionic surfactant with an HLB value within the Griffin meaning, at 25° C., greater than or equal to 8, preferably greater than or equal to 10.

The HLB (hydrophilic-lipophilic balance) value according to Griffin is defined in J. Soc. Cosm. Chem., 1954 (volume 5), pages 249-256. Reference may be made to the Kirk-Othmer Encyclopedia of Chemical Technology, volume 22, pp. 333-432, 3rd edition, 1979, Wiley, for the definition of the emulsifying properties and functions of surface-active agents, in particular pp. 347-377 of this reference.

The non-ionic surfactant(s) with an HLB value within the Griffin meaning, at 25° C., greater than or equal to 8 can be chosen from:

glycerol ethers which are preferably oxyalkylenated, in particular oxyethylenated and/or oxypropylenated, which may comprise 10 to 150 oxyethylene and/or oxypropylene units;

oxyalkylenated alcohols, in particular oxyethylenated and/or oxypropylenated alcohols, which can comprise from 7 to 150 oxyethylene and/or oxypropylene units, preferably from 20 to 100 oxyethylene units, in particular ethoxylated fatty alcohols, especially $C_8$-$C_{24}$, preferably $C_{12}$-$C_{18}$, fatty alcohols, such as ethoxylated stearyl alcohol comprising 20 oxyethylene units (CTFA name: steareth-20), such as Brij 78, sold by Uniqema, ethoxylated cetearyl alcohol comprising 30 oxyethylene units (CTFA name: ceteareth-30) and the mixture of $C_{12}$-$C_{15}$ fatty alcohols comprising 7 oxyethylene units (CTFA name: $C_{12\text{-}15}$ pareth-7), such as that sold under the name Neodol 25-7® by Shell Chemicals;

esters of fatty acid, in particular $C_8$-$C_{24}$, preferably $C_{16}$-$C_{22}$, fatty acid, and of polyethylene glycol (or PEG) (which can comprise from 1 to 150 oxyethylene units), such as PEG-50 stearate and PEG-40 monostearate, sold under the name Myrj 52P® by Uniqema;

esters of fatty acid, in particular $C_8$-$C_{24}$, preferably $C_{16}$-$C_{22}$, fatty acid, and of glycerol ethers which are preferably oxyalkylenated, in particular oxyethylenated and/or oxypropylenated (which can comprise from 10 to 150 oxyethylene and/or oxypropylene units), such as polyoxyethylenated glyceryl monostearate comprising 200 oxyethylene units, sold under the name Simulsol 220 TM® by SEPPIC; polyoxyethylenated glyceryl stearate comprising 30 oxyethylene units, such as the product Tagat S® sold by Goldschmidt, polyoxyethylenated glyceryl oleate comprising 30 oxyethylene units, such as the product Tagat O® sold by Goldschmidt, polyoxyethylenated glyceryl cocoate comprising 30 oxyethylene units, such as the product Varionic LI 13® sold by Sherex, polyoxyethylenated glyceryl isostearate comprising 30 oxyethylene units, such as the product Tagat L® sold by Goldschmidt, and polyoxyethylenated glyceryl laurate comprising 30 oxyethylene units, such as the product Tagat I® from Goldschmidt;

esters of fatty acid, in particular $C_8$-$C_{24}$, preferably $C_{16}$-$C_{22}$, fatty acid, and of sorbitol ethers which are preferably oxyalkylenated, in particular oxyethylenated and/or oxypropylenated (which can comprise from 10 to 150 oxyethylene and/or oxypropylene units), such as polysorbate 60, sold under the name Tween 60® by Uniqema;

and mixture(s) thereof.

Preferably, a composition comprises at least one non-ionic surfactant with an HLB value, within the Griffin meaning, at 25° C., greater than or equal to 8, preferably greater than or equal to 10, chosen from oxyalkylenated esters of fatty acid and of glycerol ethers. Indeed, generally, surfactants with a branched polar head group are particularly effective as emulsifying system according to the invention.

A composition according to the invention has a content of non-ionic surfactant(s) according to the invention with an HLB value, within the Griffin meaning, at 25° C., greater than or equal to 8, preferably greater than or equal to 10, which is greater than or equal to 3% by weight, relative to the total weight of the composition, preferably between 4% and 10% by weight relative to the total weight of the composition.

A composition according to the invention can comprise at least one additional surfactant, i.e. a surfactant other than a non-ionic surfactant according to the invention with an HLB value, within the Griffin meaning, at 25° C., greater than or equal to 8. This or these additional surfactant(s) can be chosen from:

non-ionic surfactant(s) having, at 25° C., an HLB balance within the Griffin meaning of less than 8, chosen from:
saccharide esters and ethers;
esters of fatty acids, in particular $C_8$-$C_{24}$ and preferably $C_{16}$-$C_{22}$ fatty acids, and of polyol, in particular of glycerol or sorbitol, preferably of glycerol;
oxyalkylenated alcohols comprising less than 10 oxyalkylene units, even better less than 5 units, in particular oxyethylene and/or oxypropylene units;
and mixtures thereof;
anionic surfactant(s), preferably having, at 25° C., an HLB value greater than or equal to 8, chosen from:
alkyl phosphates;
alkyl sulfates, in particular alkyl ether sulfates, alkylamido ether sulfates, alkylaryl polyether sulfates or monoglyceride sulfates;
alkylsulfonates, alkylamidesulfonates, alkylarylsulfonates, α-olefinsulfonates or paraffinsulfonates;
alkyl sulfosuccinates, alkyl ether sulfosuccinates or alkylamide sulfosuccinates;
alkyl sulfosuccinamates;
alkyl sulfoacetates;
acylsarcosinates, acylglutamates, acylisethionates, N-acyltaurates, acyllactylates;
alkylpolyglycoside carboxylic esters, such as alkylglucoside citrates, alkylpolyglycoside tartrates, alkylpolyglycoside sulfosuccinates or alkylpolyglycoside sulfosuccinamates; and
fatty acids, and salts thereof, in particular oleic acid, ricinoleic acid, palmitic acid or stearic acid salts, coconut oil acid or hydrogenated coconut oil acid;
alkyl-D-galactosideuronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$) alkylamido ether carboxylic acids and their salts, in particular those comprising from 2 to 50 alkylene oxide and in particular ethylene oxide groups; and mixtures thereof; preferably from fatty acid salts.

Preferably, the additional surfactant(s) is (are) chosen from non-ionic surfactant(s) having, at 25° C., within the Griffin meaning, an HLB balance less than 8.

Preferably, a composition in accordance with the invention is free of anionic surfactant(s).

The additional surfactant(s) may be present at a total content greater than or equal to 1% by weight, relative to the total weight of the composition, preferably ranging from 1.5% to 8% by weight and better still from 2% to 5% by weight, relative to the total weight of the composition.

Moreover, the emulsifying system may comprise one or more co-surfactant(s) chosen from fatty alcohols comprising from 10 to 26 carbon atoms, better still from 12 to 24 carbon atoms and even better still from 14 to 22 carbon atoms.

Anionic Associative Polymers

A composition according to the invention comprises at least one anionic associative polymer. This (these) polymer(s) perform(s) in particular a function of thickener particularly suitable for the compositions in accordance with the present invention.

Within the meaning of the present invention, the term "associative polymer" is intended to mean any amphiphilic polymer comprising at least one hydrophobic chain, therefore a fatty component, and at least one hydrophilic component.

Preferentially, the anionic associative polymer(s) according to the invention is (are) soluble in water at neutral or basic pH.

Preferably, the anionic associative polymer(s) according to the invention is (are) thus in the form of aqueous dispersions, i.e. in the form of particles of polymers dispersed in water at acidic pH.

Preferably, the anionic associative polymer(s) according to the invention is (are) not crosslinked. Preferably, the anionic associative polymer(s) according to the invention is (are) linear.

The weight-average molecular weight (Mw) of the copolymer(s) used in the cosmetic composition according to the present invention is preferably between 500 and 5 000 000 g/mol. It is more particularly between 200 000 and 2 000 000 g/mol and even more preferentially between 400 000 and 800 000 g/mol.

The anionic associative polymer(s) according to the invention is (are) preferably a block copolymer or block copolymers. Preferentially, the copolymer(s) according to the invention comprise(s) three sorts of monomers, also called terpolymers.

The anionic associative polymer(s) used in the present invention comprise(s):
at least one backbone chain, or backbone, preferably just one, derived from at least one monomer comprising at least one carboxylic acid and at least one α,β-monoethylenic unsaturation, an ester or esters thereof, a salt or salts thereof, and a mixture thereof,
at least one hydrophobic chain, preferably a hydrophobic graft, which extends laterally relative to the backbone,
at least one alkoxylated or glycerolated spacer linking said backbone chain and said hydrophobic chain(s).

Preferentially, the anionic associative polymer(s) used in the present invention comprise(s) a backbone chain derived from at least one monomer of (meth)acrylic acid, an ester or esters thereof, a salt or salts thereof, and a mixture thereof. Thus, the anionic associative polymer(s) used in the present invention comprise(s) a backbone chain derived from at least one monomer of acrylic acid, of methacrylic acid, an ester or esters thereof, a salt or salts thereof, and a mixture thereof.

The hydrophobic chain(s) may be low in number with respect to the backbone. It (they) may be laterally distributed randomly (random copolymers) or preferably in the form of blocks, or of grafts (block copolymers), preferably in the form of blocks.

The hydrophobic chain(s) preferably comprise(s) a linear and saturated $C_8$-$C_{24}$, preferably $C_{12}$-$C_{20}$, more preferentially $C_{16}$-$C_{22}$, fatty chain. This (these) hydrophobic chain(s) preferably comprise(s) a $C_8$-$C_{24}$, preferably $C_{12}$-$C_{20}$, more preferentially $C_{16}$-$C_{22}$, fatty alcohol or fatty acid. Preferably, the hydrophobic chain(s) is (are) chosen from a stearyl group, a behenyl group, and a mixture thereof, in particular from stearyl alcohol and behenyl alcohol.

Said hydrophobic chain(s) and its (their) respective spacer preferably extend, in continuity with respect to one another, laterally relative to said backbone chain. The spacer directly or indirectly links said backbone and said hydrophobic chain.

Preferably, the spacer(s) is (are) hydrophilic. This (these) spacer(s) comprise(s) $C_2$-$C_8$, preferably $C_2$, alkoxyl groups.

Advantageously, it (they) comprise(s) between 15 and 50 alkoxyl groups, preferably from 15 to 50 oxyethylene groups. Preferentially, it (they) comprise(s) 20 or 25 alkoxyl groups, preferably 20 or 25 oxyethylene groups.

The spacer(s) and the hydrophobic chain(s) advantageously together form a $C_2$-$C_8$, preferably $C_2$, alkoxylated ether of $C_8$-$C_{24}$, preferably $C_{12}$-$C_{22}$, more preferentially $C_{16}$-$C_{22}$, fatty alcohols, or an alkoxylated ester of a $C_8$-$C_{24}$, $C_{12}$-$C_{22}$, more preferentially $C_{16}$-$C_{22}$, fatty acid, preferably a $C_2$-$C_8$, preferably $C_2$, alkoxylated ether of $C_8$-$C_{24}$, preferably $C_{12}$-$C_{22}$, more preferentially $C_{16}$-$C_{22}$, fatty alcohols.

This alkoxylated ether of a fatty alcohol or this alkoxylated ester of a fatty acid preferably comprises from 15 to 50 alkoxylated groups, preferably from 15 to 50 oxyethylene groups.

Preferably, said alkoxylated ether of a fatty alcohol is chosen from said oxyethylenated ether of stearyl alcohol comprising 20 oxyethylene groups and said oxyethylenated ether of behenyl alcohol comprising 25 oxyethylene groups.

Preferably, said alkoxylated ester of a fatty acid is chosen from said oxyethylenated ester of stearic acid, for example comprising 40 oxyethylene groups, also known as PEG-40 stearate.

According to one particular embodiment, the hydrophilic spacer and the hydrophobic chain are linked, before polymerization, by esterification with a (meth)acrylic acid.

According to one embodiment variant, the hydrophilic spacer and the hydrophobic chain can be linked to the backbone chain after polymerization of the backbone chain, by random esterification of said backbone chain.

Among the anionic associative polymer(s) according to the invention, mention may be made of:
copolymers derived from (meth)acrylic acid/$C_1$-$C_8$, better still $C_1$-$C_3$, preferably $C_2$, alkyl (meth)acrylate/$C_8$-$C_{24}$, better still $C_{12}$-$C_{22}$, preferably $C_{16}$-$C_{22}$, even more preferentially $C_{18}$ or $C_{22}$, fatty alcohol (meth)acrylate, and a mixture thereof, which is alkoxylated or glycerolated, such as the Aculyn products sold by the company Rohm & Haas.

In particular, among the anionic associative polymers, preference is given to:
copolymers derived from acrylic acid/ethyl acrylate/stearyl methacrylate which is polyoxyethylenated, for example with 20 mol of ethylene oxide, such as the product sold under the name Aculyn 22® by the company Rohm & Haas;
copolymers derived from acrylic acid/ethyl acrylate/behenyl methacrylate which is polyoxyethylenated, for example with 25 mol of ethylene oxide, such as the product sold under the name Aculyn 28® by the company Rohm & Haas;
and a mixture thereof.

Preferably, the anionic associative polymer(s) according to the invention is (are) chosen from the copolymers having the following INCI names: Acrylates/Steareth-20 Methacrylate Copolymer, Acrylates/Beheneth-25 Methacrylate Copolymer, and a mixture thereof.

The total content of anionic associative polymer(s) is greater than or equal to 0.05% by weight, better still greater than or equal to 0.1% by weight, relative to the total weight of the composition, preferably inclusively between 0.1% and 1% by weight, more preferentially between 0.2% and 0.8% by weight relative to the total weight of the composition.

The total content of anionic associative polymer(s) and the total content of emulsifying system, and in particular of non-ionic surfactant(s) with an HLB value at 25° C. greater than or equal to 8, or even greater than or equal to 10, are such that the weight ratio of anionic associative polymer(s) to said emulsifying system is greater than or equal to 1/60, preferably between 1/50 and 1/2, preferably inclusively between 1/40 and 1/3, more preferentially between 1/30 and 1/5.

Particles

The compositions according to the present invention comprise particles of hard wax(es) and preferably of film-forming polymer(s), preferentially both present in the form of an aqueous dispersion or aqueous dispersions.

These particles can be characterized by an average particle size. Such particles are generally isotropic, in particular with a substantially spherical shape or spherical shape.

Particle Size

A particle size can be measured by various techniques. Mention may in particular be made of (dynamic and static) light scattering techniques, Coulter capture techniques, measurements of sedimentation rate (related to the size via Stokes law) and microscopy.

These techniques make it possible to measure a particle diameter, and for some particles, a particle size distribution.

Preferably, the sizes and the size distributions of the particles of the compositions according to the invention are measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., "Light Scattering by Small Particles", Chapters 9 and 10, Wiley, N.Y., 1957.

In the context of the present invention, the "average particle size" is expressed as volume-average "effective" diameter D[4,3], defined in the following way:

$$D[4,3] = \frac{\sum_i V_i \cdot d_i}{\sum_i V_i}$$

where $V_i$ represents the volume of the particles of effective diameter $d_i$. This parameter is in particular described in the technical documentation of the particle size analyser.

The measurements are carried out at 25° C., on a dilute particle dispersion. The "effective" diameter is obtained by taking a refractive index of 1.33 for water and an average refractive index of 1.45 for the particles.

Thus, preferentially, the particles of the compositions in accordance with the invention, comprising at least one hard wax and preferably at least one film-forming polymer, preferentially present in the form of aqueous dispersions, have an average size, expressed as volume-average "effective" diameter D[4,3], of less than or equal to 5 µm, in particular strictly less than 5 µm, more preferentially than 2 µm, and even more preferentially less than or equal to 1 µm. Such particle sizes preferentially correspond to the size of the particles in the final composition.

This average particle size is advantageous in terms of the use of the composition in accordance with the present invention compared with compositions comprising particles of hard waxes and of film-forming polymers of larger sizes which result in a mascara that is difficult or even impossible to formulate, granular, too thick, impossible to apply (too compact and non-disintegrable) and uncomfortable, that exhibits a poor dispersion of the pigments and fillers, and that has a matt colour.

It is understood that the emulsifying system(s) will have a tendency to be positioned at the interface of the aqueous phase and of the particles of hard waxes, and optionally of the particles of film-forming polymers, so as to stabilize them. The particle sizes measured are therefore done so in the presence of the surfactant(s), since the latter are difficult to dissociate from the particles. The sizes measured and given take into account this particularity.

With regard to the other particles of the composition, for example colorants and fillers, these compounds will be dealt with independently in another section of the description, the size characteristics of particles of this type diverging in comparison with the particle sizes of the waxes and film-forming polymers in accordance with the invention.

The particles are advantageously present in a composition in accordance with the invention at a content greater than or equal to 30% by weight relative to the total weight of the composition, better still ranging from 35% to 60% by weight relative to the total weight of the composition.

Wax(es)

The wax(es) is (are) in general a lipophilic compound that is solid at ambient temperature (25° C.), with a reversible solid/liquid change in state, having a melting point of greater than or equal to 30° C., which may be up to 200° C. and in particular up to 120° C.

Within the meaning of the invention, the melting point corresponds to the temperature of the most endothermic peak observed in thermal analysis (DSC) as described in Standard ISO 11357-3; 1999. The melting point of the wax can be measured using a differential scanning calorimeter (DSC), for example the calorimeter sold under the name DSC Q2000 by the company TA Instruments.

Preferably, the waxes exhibit an enthalpy of fusion ΔHf of greater than or equal to 70 J/g.

Preferably, the waxes comprise at least one crystallizable part, which is visible by X-ray observation.

The measurement protocol is as follows:

A sample of 5 mg of wax placed in a crucible is subjected to a first temperature rise passing from −20° C. to 120° C. at a heating rate of 10° C./minute, is then cooled from 120° C. to −20° C. at a cooling rate of 10° C./minute and is finally subjected to a second temperature rise passing from −20° C. to 120° C. at a heating rate of 5° C./minute. During the second temperature rise, the following parameters are measured:

the melting point (M.p.) of the wax, as mentioned above corresponding to the temperature of the most endothermic peak of the melting curve observed, representing the variation of the difference in power absorbed as a function of the temperature, ΔHf: the enthalpy of fusion of the wax, corresponding to the integral of the entire melting curve obtained. This enthalpy of fusion of the wax is the amount of energy necessary to make the compound change from the solid state to the liquid state. It is expressed in J/g.

The wax(es) can be hydrocarbon-based wax(es), fluoro wax(es) and/or silicone wax(es) and can be of vegetable, mineral, animal and/or synthetic origin.

The wax(es) may be present at a total content greater than or equal to 10% by weight relative to the total weight of the composition, better still 15% by weight relative to the total weight of the composition. Preferably, it is (they are) present at a content ranging from 10% to 30% by weight relative to the total weight of the composition, better still from 15% to 30% by weight. A composition according to the invention comprises at least one hard wax, preferably present in the preparation of the composition in the form of an aqueous dispersion of particle(s) of wax(es).

Hard Wax

According to the invention, the composition comprises more specifically at least one hard wax.

For the purposes of the present invention, the term "hard wax" is understood to mean a wax which has a melting point greater than or equal to 60° C., in particular ranging from 65 to 120° C., more preferentially between 70 and 100° C.

Advantageously, for the purposes of the present invention, the term "hard wax" is understood to mean a wax exhibiting, at 20° C., a hardness of greater than 5 MPa, in particular ranging from 5 to 30 MPa, preferably of greater than 6 MPa, better still ranging from 6 to 25 MPa.

To carry out these hardness measurements, the wax is melted at a temperature equal to the melting point of the wax+20° C. For this, 30 g of wax are placed in a 100 ml beaker with a diameter equal to 50 ml, which is itself placed on a magnetic stirrer hotplate.

An amount of approximately 15 g of molten wax is poured into a stainless steel vessel 80 mm in diameter and 15 mm deep, preheated to 45° C. in an oven. The wax is then left to recrystallize in a thermostated room at 20° C. for 24 hours before carrying out the measurement.

The mechanical properties of the wax or of the mixture of waxes are determined in a thermostated room at 20° C. using the texture analyser sold under the name TA-XT2i by the company Swantech, equipped with a stainless-steel cylinder having a diameter of 2 mm.

The measurement comprises 3 steps: a first step after automatic detection of the surface of the sample in which the spindle moves at the measuring speed of 0.1 mm/s, and penetrates the wax to a penetration depth of 0.3 mm, and the software notes the value of the maximum force attained; a second step, referred to as relaxation step, in which the spindle remains at this position for one second and in which the force is noted after 1 second of relaxation; finally, a 3rd step, referred to as withdrawal step, in which the spindle returns to its initial position at the speed of 1 mm/s and the probe withdrawal energy (negative force) is noted.

The value of the hardness is the maximum compressive force measured in newtons, divided by the surface area of the cylinder of the texture analyser in $mm^2$ in contact with the wax. The hardness value obtained is expressed in megapascals or MPa.

By way of examples of hard wax, mention may in particular be made of carnauba wax, candelilla wax, bis-PEG-12 dimethicone candelillate, for instance the Siliconyl Candellila Wax sold by the company Koster Keunen, hydrogenated Jojoba wax, for instance the product sold by the company Desert Whale, hydrogenated palm oil, such as the product sold by the company SIO, rice bran wax, sumach wax, ceresin wax, laurel wax, Chinese insect wax, shellac wax, hydrogenated olive oil, such as Waxolive from the company Soliance, waxes obtained by hydrogenation of olive oil esterified with fatty alcohols comprising a C12 to C18 chain, such as those sold by the company Sophim under the trade names Phytowax Olive 12L44, 14L48, 16L55 and 18L57, waxes obtained by hydrogenation of castor oil esterified with cetyl or behenyl alcohol, for instance those which are sold under the names Phytowax Ricin 16 L 64 and Phytowax Ricin 22 L 73 by the company Sophim, hydrogenated cameline wax, ouricury wax, montan wax, ozokerite waxes, for instance the Wax SP 1020 P sold by the company Strahl & Pitsch, microcrystalline waxes, for example the product sold under the trade name Microwax HW by the company Paramelt, triglycerides of lauric, palmitic, cetylic and stearic acids (INCI name: hydrogenated coco glycerides) for instance the product sold under the trade name Softisan 100 by the company Sasol, polymethylene waxes, for instance the product sold under the trade name Cirebelle 303 by the company Sasol, polyethylene waxes, for instance the products sold under the trade names Performalene 400 polyethylene, Performalene 655 polyethylene and Performalene 500-L polyethylene by the company New Phase Technologies, alcool-polyethylene waxes, for instance the product sold under the name Performacol 425 Alcohol by the company Bareco, the ethylene/acrylic acid 95/5 copolymer sold under the trade name AC 540 wax by the company Honeywell, hydroxyoctacosanyl hydroxystearate, for instance the product sold under the trade name l'Elfacos C 26 by the company Akzo, octacosanyl stearate, for instance the product sold under the name Kester Wax K 82 H by the company Koster Keunen, stearyl stearate, for instance the product sold under the name Liponate SS by the company Lipo Chemicals, pentaerythrityl distearate, for instance the product sold under the name Cutina PES by the company Cognis, the mixture of dibehenyl adipate, dioctadecyl adipate and dieicosanyl adipate (INCI name: C18-22 dialkyl adipate), the mixture of dilauryl adipate and ditetradecyl adipate (INCI name: C12-14 dialkyl adipate), the mixture of dioctadecyl sebacate, didocosyl sebacate and dieicosyl sebacate (INCI name: C18-22 dialkyl sebacate), the mixture of dioctadecyl octadecanedioate, didocosyl octanedioate and dieicosyl octanedioate (INCI name: C18-22 dialkyl octanedioate), for instance those sold by the company Cognis, pentaerythrityl tetrastearate, for instance Liponate PS-4 from the company Lipo Chemicals, tetracontanyl stearate, for instance Kester Wax K76 H from the company Koster Keunen, stearyl benzoate, for instance Finsolv 116 from the company Finetex, behenyl fumarate, for instance Marrix 222 from the company Akzo Bernel, di(triméthylol-1,1,1-propane) tetrastearate, for instance the product which is provided under the name Hest 2T-4S by the company Heterene, didotriacontanyl distearate, for instance Kester Wax K82D from the company Koster Keunen, polyethylene glycol montanate comprising 4 oxyethylene units (PEG-4), for instance the product sold under the name Clariant Licowax KST1, hexanediol disalycilate, for instance Betawax RX-13750 sold by the company CP Hall, dipentaerythrytyl hexastearate, for instance the product which is sold under the trade name Hest 2P-6S by the company Heterene, ditrimethylolpropane tetrabehenate, for instance the product which is sold under the trade name Hest 2T-4B by the company Heterene, Jojoba esters, for instance the product which is sold under the trade name Floraester HIP by the company Floratech, mixtures of (C20-C40) linear carboxylic acid/saturated hydrocarbons (INCI name: C20-C40 acid polyethylene), for instance Performacid 350 acid from the company New Phase Technologies, synthetic wax of Fischer-Tropsch type, such as the product sold under the reference Rosswax 100 by the company Ross, stearyl alcohol, behenyl alcohol, dioctadecyl carbonate, for instance Cutina KE 3737, sucrose polybehenate, for example Crodaderm B from the company Croda, and mixtures thereof.

Use may also be made of the waxes described above in the form of commercially available mixtures, for example, under the names Koster KPC-56 (mixture of 87.5% by weight of cetyl stearate, 7.5% by weight of behenyl alcohol and 5% by weight of palm kernel glycerides), KPC-60 (mixture of 87.5% by weight of stearyl stearate, 7.5% by weight of behenyl alcohol and 5% by weight of palm kernel glycerides), KPC-63 (mixture of 87.5% by weight of behenyl stearate, 7.5% by weight of behenyl alcohol and 5% by weight of palm kernel glycerides) and KPC-80 (mixture of 86% by weight of synthetic beeswax, 7.5% of hydrogenated vegetable oil and 6.5% by weight of behenyl alcohol) from the company Koster Keunen.

Use is preferably made of waxes of vegetable origin, such as carnauba wax, candelilla wax, hydrogenated jojoba wax, sumach wax, waxes obtained by hydrogenation of olive oil esterified with fatty alcohols comprising a C12 to C18 chain sold by the company Sophim in the Phytowax range (12L44, 14L48, 16L55 and 18L57), rice bran wax, stearyl and behenyl alcohols, laurel wax or ouricury wax.

Preferably, the particles of waxes used in the preparation of a composition in accordance with the present invention are not introduced in the form of a microdispersion of preprepared hard waxes, as described in patent applications FR 2 687 569 or FR 2 815 849. Indeed, the hard wax(es) used in a composition in accordance with the present invention is (are) introduced in the form of powder or a solid fatty substance. However, the final composition can be defined as comprising an aqueous dispersion of hard wax(es). Indeed, according to the present method of production, the dispersion of hard wax(es) is carried out in situ, making it possible, surprisingly and advantageously, to achieve high solids contents and high contents of hard wax(es) which would be unattainable if a preprepared microdispersion of hard waxes was introduced as it is in order to produce a cosmetic composition according to the invention. Indeed, in the present invention, the water resulting from the aqueous dispersion of the film-forming polymer(s) serves to carry out the dispersion of the hard wax(es).

The hard wax(es) is (are) preferably polar.

For the purposes of the present invention, the term "polar wax" is understood to mean a wax for which the solubility parameter calculated beyond its melting point $\delta_a$ is other than 0 $(J/cm^3)^{1/2}$.

In particular, the term "polar wax" is understood to mean a wax for which the chemical structure is formed essentially of, indeed even consists of, carbon and hydrogen atoms and comprises at least one highly electronegative heteroatom, such as an oxygen, nitrogen, silicon or phosphorus atom.

The definition and calculation of the solubility parameters in the Hansen three-dimensional solubility space are described in the paper by C. M. Hansen: "The three-dimensional solubility parameters", J. Paint Technol., 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$ The parameters $\delta_p$, $\delta_h$, $\delta_D$ and $\delta_a$ are expressed in $(J/cm^3)^{1/2}$.

The composition according to the invention comprises a content of hard wax(es), preferentially present in the form of an aqueous dispersion, greater than or equal to 10% by weight relative to the total weight of the composition, better still greater than or equal to 15% by weight relative to the total weight of the composition.

More generally, the composition according to the invention advantageously comprises a total content of hard wax(es), preferentially present in the form of an aqueous dispersion, ranging from 10% to 30% by weight, better still from 15% to 30% by weight, relative to the total weight of the composition.

According to one advantageous embodiment, the composition according to the invention comprises a total content of particles of hard wax(es), preferentially present in the form of an aqueous dispersion, representing at least 80% by weight, preferentially at least 90% by weight and more preferentially 100% by weight, relative to the total weight of wax(es).

Preferably, the total content of hard wax(es), preferentially present in the form of an aqueous dispersion, is greater than or equal to 30% by weight and preferentially greater than or equal to 40% by weight, relative to the total weight of the solid particles.

According to one advantageous embodiment, the total content of hard wax(es), preferentially present in the form of an aqueous dispersion, represents at least 80% by weight, preferentially at least 90% by weight and more preferentially 100% by weight, relative to the total weight of fatty substances.

Additionally, a composition according to the invention may comprise at least one soft wax, optionally present in the form of an aqueous dispersion of particles of wax(es), i.e. a wax of which the melting point is strictly below 50° C. and optionally of which the hardness is strictly less than 5 MPa.

However, a composition according to the invention preferably comprises less than 5% by weight of soft wax(es), preferably less than 2% by weight of soft wax(es) and even more preferentially is free of soft wax(es).

The total content of anionic associative polymer(s) and the total content of wax(es) are such that the weight ratio of anionic associative polymer(s) to wax(es) is greater than or equal to 1/250, preferably inclusively between 1/200 and 1/20, more preferentially between 1/150 and 1/50.

Film-Forming Polymer(s)

The composition according to the invention preferably comprises at least one aqueous dispersion of particles of film-forming polymer(s) and optionally at least one additional film-forming polymer (not present in the form of an aqueous dispersion of particles, such as a water-soluble, film-forming polymer).

In the present application, the term "film-forming polymer" is understood to mean a polymer which is capable, by itself alone or in the presence of an additional film-forming agent, of forming a macroscopically continuous deposited layer and preferably a cohesive deposited layer, better still a deposited layer having cohesive and mechanical properties such that said deposited layer can be isolated and handled in isolation, for example when said deposited layer is prepared by pouring onto a non-stick surface, such as a Teflon-coated or silicone-coated surface.

A composition according to the invention preferably comprises a total dry matter content in terms of film-forming polymer(s) greater than or equal to 5% by weight, preferably greater than or equal to 10% by weight, relative to the total weight of the composition, better still greater than or equal to 12% by weight, relative to the total weight of the composition.

A composition according to the invention preferably comprises a total dry matter content in terms of film-forming polymer(s) ranging from 10% to 30% by weight, relative to the total weight of the composition, better still from 12% to 25%.

The composition according to the invention preferably comprises more specifically at least one aqueous dispersion of particles formed from one or more film-forming polymers.

It can also comprise at least one water-soluble, film-forming polymer. Thus, a composition can comprise at least one additional film-forming polymer which is distinct from particles of film-forming polymer(s) present in the form of an aqueous dispersion. The content of this (these) additional film-forming polymer(s), termed water-soluble, is preferably less than or equal to 10% by weight, relative to the total weight of the composition, even more preferentially less than or equal to 5% by weight, better still less than or equal to 2% by weight, relative to the total weight of the composition.

Film-Forming Polymer(s) as an Aqueous Dispersion

Such a film-forming polymer, present in said preparation of the composition in the form of particles as an aqueous dispersion, is generally known as a (pseudo)latex, i.e. latex or pseudolatex. The techniques for preparing these dispersions are well known to those skilled in the art.

A dispersion suitable for the invention can comprise one or more types of particles, it being possible for these particles to vary in terms of their size, their structure and/or their chemical nature.

A composition according to the invention comprises a total dry matter content in terms of particles of film-forming polymer(s), in the form of an aqueous dispersion, greater than or equal to 10% by weight.

Advantageously, a composition according to the invention comprises a total dry matter content in terms of particles of film-forming polymer(s), in the form of an aqueous dispersion, greater than or equal to 12% by weight, relative to the total weight of the composition, preferably greater than or equal to 15% by weight, relative to the total weight of the composition.

A composition according to the invention preferably comprises a total dry matter content in terms of particles of film-forming polymer(s) ranging from 10% to 30% by weight, relative to the total weight of the composition, better still from 12% to 25% by weight.

The total content of particles of film-forming polymer(s), present in the form of an aqueous dispersion or aqueous dispersions, is preferably greater than or equal to 30% by weight and preferentially greater than or equal to 40% by weight, relative to the total weight of the particles.

These particles may be of anionic, catatonic or neutral nature and may constitute a mixture of particles of various natures.

Mention may be made, among the film-forming polymers which can be used in the composition of the present invention, of synthetic polymers, of free-radical type or of polycondensate type, polymers of natural origin and mixtures thereof. Generally, these polymers may be random polymers, block copolymers of type A-B, multiblock A-B-A or else ABCD, etc, or even grafted polymers.

Free-Radical Film-Forming Polymer

The term "free-radical polymer" is understood to mean a polymer obtained by polymerization of unsaturated and in particular ethylenically unsaturated monomers, each monomer being capable of homopolymerizing (unlike polycondensates).

The film-forming polymers of free-radical type may in particular be acrylic and/or vinyl homopolymers or copolymers.

The vinyl film-forming polymers may result from the polymerization of ethylenically unsaturated monomers containing at least one acid group and/or esters of these acid monomers and/or amides of these acid monomers.

Ethylenically unsaturated monomers having at least one acid group or acid-group-bearing monomer that may be used include α,β-ethylenically unsaturated carboxylic acids such as acrylic acid, methacrylic acid, crotonic acid, maleic acid or itaconic acid. (Meth)acrylic acid and crotonic acid are particularly used, and more particularly (meth)acrylic acid.

The esters of acidic monomers are advantageously chosen from (meth)acrylic acid esters (also known as (meth)acrylates), in particular (meth)acrylates of an alkyl, in particular of a $C_1$-$C_{20}$ and preferably $C_1$-$C_8$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate and lauryl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters are in particular alkyl (meth)acrylates.

According to the present invention, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, and in particular N-alkyl (meth)acrylamides, in particular of a $C_2$-$C_{12}$ alkyl. Among the N-alkyl(meth)acrylamides that may be mentioned are N-ethylacrylamide, N-t-butylacrylamide and N-t-octylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned previously.

Examples of vinyl esters that may be mentioned are vinyl acetate, vinyl neodecanoate, vinyl pivalate, vinyl benzoate and vinyl t-butylbenzoate.

Styrene monomers that may be mentioned include styrene and α-methylstyrene.

The list of monomers given is not limiting, and it is possible to use any monomer known to those skilled in the art included in the categories of acrylic and vinyl monomers (including monomers modified with a silicone chain).

As vinyl polymer, use may also be made of silicone-comprising acrylic polymers.

Mention may also be made of the polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers".

Polycondensate

As film-forming polymer of polycondensate type, mention may be made of anionic, cationic, non-ionic or amphoteric polyurethanes, polyurethane-acrylics, polyurethane-polyvinylpyrrolidones, polyester-polyurethanes, polyether-polyurethanes, polyureas, polyurea/polyurethanes, silicone polyurethanes, and mixtures thereof.

The film-forming polyurethane may be, for example, an aliphatic, cycloaliphatic or aromatic polyurethane, polyurea/urethane or polyurea copolymer comprising, alone or as a mixture, at least one block chosen from:
 a block of aliphatic and/or cycloaliphatic and/or aromatic polyester origin, and/or
 a branched or non-branched silicone block, for example polydimethylsiloxane or polymethylphenylsiloxane, and/or
 a block comprising fluoro groups.

The film-forming polyurethanes as defined in the invention may also be obtained from branched or non-branched polyesters or from alkyds comprising labile hydrogens, which are modified by reaction with a diisocyanate and a difunctional organic compound (for example dihydroxy, diamino or hydroxyamino), also comprising either a carboxylic acid or carboxylate group, or a sulfonic acid or sulfonate group, or alternatively a neutralizable tertiary amine group or a quaternary ammonium group.

Among the film-forming polycondensates, mention may also be made of polyesters, polyesteramides, fatty-chain polyesters, polyamides and epoxyester resins.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, 2,6-naphthalenedicarboxylic acid. These dicarboxylic acid monomers may be used alone or as a combination of at least two dicarboxylic acid monomers. Among these monomers, phthalic acid, isophthalic acid and terephthalic acid are in particular chosen.

The diol may be chosen from aliphatic, alicyclic and aromatic diols. Use is in particular made of a diol chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

Polymer of Natural Origin

In the present invention, use may be made of polymers of natural origin which are optionally modified, for instance shellac resin, gum sandarac, dammars, elemis, copals, water-insoluble cellulose-based polymers, such as nitrocellulose, modified cellulose esters, including in particular, carboxyalkylcellulose esters, such as those described in patent application US 2003/185774, and mixtures thereof.

According to one particular embodiment of the invention, said at least one film-forming polymer in the dispersed state is chosen from acrylic polymer dispersions, polyurethane dispersions, sulfopolyester dispersions, vinyl dispersions, polyvinyl acetate dispersions, vinylpyrrolidone/dimethylaminopropylmethacrylamide/lauryldimethylpropylmethacrylamido ammonium chloride terpolymer dispersions, polyurethane/polyacrylic hybrid polymer dispersions, dispersions of particles of core-shell type, and mixtures thereof.

Various types of aqueous dispersions, which are in particular commercially available, which are suitable for preparing the composition in accordance with the present invention, are detailed hereinafter.

1/ Thus, according to one preferred embodiment of the invention, the aqueous dispersion of particles of polymer is an aqueous dispersion of acrylic polymer.

In particular, the acrylic polymer may be a styrene/acrylate copolymer, and in particular a polymer chosen from copolymers derived from the polymerization of at least one styrene monomer and at least one $C_1$-$C_{18}$ alkyl (meth)acrylate monomer.

As styrene monomers that may be used in the invention, mention may be made, for example, of styrene or α-methylstyrene, and in particular styrene.

The $C_1$-$C_{18}$ alkyl (meth)acrylate monomer is in particular a $C_1$-$C_{12}$ alkyl (meth)acrylate and more particularly a $C_1$-$C_{10}$ alkyl (meth)acrylate. The $C_1$-$C_{18}$ alkyl (meth)acrylate monomer may be chosen from methyl acrylate, methyl methacrylate, ethyl acrylate, propyl acrylate, butyl acrylate, butyl methacrylate, hexyl acrylate, octyl acrylate, 2-ethylhexyl acrylate, lauryl (meth)acrylate and stearyl (meth)acrylate.

Use may be made according to the invention, as acrylic polymer in aqueous dispersion, of the styrene/acrylate copolymer sold under the name Joncryl SCX-8211® by the company BASF or Syntran 5760CG by the company Interpolymer, the acrylic polymer sold under the reference Acronal® DS-6250 by the company BASF or the acrylic copolymer Joncryl® 95 from the company BASF.

2/ According to one variation of embodiment of the invention, the aqueous dispersion of particles of polymer is an aqueous dispersion of particles of polyester-polyurethane and/or of polyether-polyurethane which is in particular anionic.

The anionic nature of the polyester-polyurethanes and of the polyether-polyurethanes used according to the invention is due to the presence, in their constituent units, of groups comprising a carboxylic acid or sulfonic acid function.

The particles of polyester-polyurethanes or of polyether polyurethanes that are used according to the invention are generally sold in the form of aqueous dispersions.

The particle content of said dispersions currently available on the market ranges from approximately 20% to approximately 60% by weight relative to the total weight of the dispersion.

Among the anionic polyester-polyurethane dispersions that can be used in the compositions according to the invention, mention may particularly be made of the product sold under the name Avalure UR 405® by the company Noveon or Baycusan 01004 by the company Bayer Material Science.

Among the dispersions of particles of anionic polyether-polyurethane that can be used according to the invention, mention may particularly be made of those sold under the name Avalure UR 450® by the company Noveon and under the name Neorez R 970® by the company DSM.

According to one particular embodiment of the invention, use may be made of a mixture of commercial dispersions consisting of particles of anionic polyester polyurethane, as defined above, and of particles of anionic polyether-polyurethane, also defined above.

For example, use may be made of a mixture consisting of the dispersion sold under the name Sancure 861® or a mixture of the product sold under the name Avalure UR 405® and of the product sold under the name Avalure UR 450®, these dispersions being sold by the company Noveon.

3/ According to another particular embodiment of the invention, the aqueous dispersion used comprises a mixture of at least two film-forming polymers in the form of particles which are distinct in terms of their respective glass transition temperatures (Tg).

In particular, according to one embodiment of the invention, the composition in accordance with the invention may comprise at least one first film-forming polymer in the dispersed state and at least one second film-forming polymer in the dispersed state, said first and second polymers having different Tgs, and preferably the Tg of the first polymer (Tg1) is higher than the Tg of the second polymer (Tg2). In particular, the difference between Tg1 and Tg2 is, in absolute value, at least 10° C., preferably at least 20° C.

More specifically, it comprises, in an acceptable aqueous medium:

a) particles, dispersed in the aqueous medium, of a first film-forming polymer having at least one glass transition temperature Tg1 greater than or equal to 20° C., and b) particles, dispersed in the aqueous medium, of a second film-forming polymer having at least one glass transition temperature Tg2 less than or equal to 70° C.

This dispersion generally results from a mixture of two aqueous dispersions of film-forming polymer.

The first film-forming polymer has at least one, in particular has one, glass transition temperature Tg1 greater than or equal to 20° C., in particular ranging from 20° C. to 150° C., and advantageously greater than or equal to 40° C., in particular ranging from 40° C. to 150° C., and in particular greater than or equal to 50° C., in particular ranging from 50° C. to 150° C.

The second film-forming polymer has at least one, in particular has one, glass transition temperature Tg2 less than or equal to 70° C., in particular ranging from −120° C. to 70° C., and in particular less than 50° C., in particular ranging from −60° C. to +50° C., and more particularly ranging from −30° C. to 30° C.

The measurement of the glass transition temperature (Tg) of a polymer is carried out by DMTA (Dynamical and Mechanical Temperature Analysis) as described below.

To measure the glass transition temperature (Tg) of a polymer, viscoelasticimetry tests are carried out with a DMTA apparatus from Polymer laboratories, on a sample of film. This film is prepared by casting the aqueous dispersion of film-forming polymer in a teflon-coated template and then dried at 120° C. for 24 hours. A film is then obtained, from which test specimens are cut (for example using a hole punch). These test specimens are typically approximately 150 μm thick, from 5 to 10 mm wide and have a useful length of about 10 to 15 mm. This sample is subjected to a tensile stress. The sample is subjected to a static force of 0.01 N on which is superposed a sinusoidal displacement of +/−8 μm at a frequency of 1 Hz. The operation is thus carried out in the linear range, at low levels of strain. This tensile stress is applied to the sample at temperatures ranging from −150° C. to +200° C. with a temperature variation of 3° C. per minute.

The complex modulus $E^*=E'+iE''$ of the polymer tested is then measured as a function of the temperature.

From these measurements, the dynamic moduli E', E" and the damping power: $tg\delta=E''/E'$ are deduced.

Next, the curve of the tgδ values as a function of the temperature is plotted; this curve exhibits at least one peak. The glass transition temperature Tg of the polymer corresponds to the temperature at which the top of this peak lies.

When the curve has at least 2 peaks (in this case, the polymer has at least 2 Tgs), the Tg value of the polymer tested is taken as the temperature for which the curve exhibits a peak of highest amplitude (i.e. corresponding to the largest value of tgδ; in this case, only the "predominant" Tg is considered as the Tg value of the polymer tested).

In the present invention, the transition temperature Tg1 corresponds to the "predominant" Tg (within the meaning previously defined) of the first film-forming polymer when the latter has at least 2 Tgs; the glass transition temperature Tg2 corresponds to the "predominant" Tg of the second film-forming polymer when the latter has at least 2 Tgs.

The first film-forming polymer and the second film-forming polymer can be chosen, independently of one another, from free-radical polymers, polycondensates and polymers of natural origin, as previously defined, having the glass transition temperature characteristics previously defined.

As first film-forming polymer in an aqueous dispersion, use may be made of the aqueous dispersions of polymer sold under the names NeoRez R-989® by the company DSM, Joncryl 95 and Joncryl®8211 by the company BASF.

As second film-forming polymer in an aqueous dispersion, use may be made, for example, of the aqueous dispersions of polymer sold under the names Avalure® UR-405 and Avalure® UR-460 by the company Noveon, Acrilem IC89RT® by the company ICAP or Neocryl A-45 by the company DSM.

The film-forming polymer of the Avalure® UR-460 aqueous dispersion is a polyurethane obtained by polycondensation of poly(tetramethylene oxide), of tetramethylxylylene diisocyanate, of isophorone diisocyanate and of dimethylolpropionic acid.

According to one most particularly preferred embodiment of the invention, the combination of styrene/acrylate polymer dispersion such as the dispersion sold under the reference Joncryl 8211® by BASF and of acrylic polymer dispersion such as the dispersion sold under the reference Neocryl A-45® by DSM is used as first and second film-forming polymers in an aqueous dispersion.

According to another preferred embodiment of this particular embodiment of point 3/ above of the invention, a dispersion of acrylic polymer such as the dispersion sold under the reference Joncryl 95® by BASF is used as first film-forming polymer in an aqueous dispersion and a dispersion of anionic polyurethane polymer sold under the reference Avalure UR405® by DSM is used as second film-forming polymer.

As aqueous dispersions of film-forming polymer, use may be made of:
the acrylic dispersions sold under the names Acronal DS-6250® by the company BASF, Neocryl A-45®, Neocryl XK-90®, Neocryl A-1070®, Neocryl A-1090®, Neocryl BT-62®, Neocryl A-1079® and Neocryl A-523® by the company DSM, Joncryl 95® and Joncryl 8211® by the company BASF, Daitosol 5000 AD® or Daitosol 5000 SJ by the company Daito Kasey Kogyo; Syntran 5760 CG by the company Interpolymer,
the aqueous dispersions of polyurethane sold under the names Neorez R-981® and Neorez R-974® by the company DSM, Avalure UR-405®, Avalure UR-410®, Avalure UR-425®, Avalure UR-450®, Sancure 875®, Avalure UR 445® and Avalure UR 450® by the company Noveon, Impranil 85® by the company Bayer and Baycusan C1004® by the company Bayer Material Science,
the sulfopolyesters sold under the trade name Eastman AQ® by the company EASTMAN CHEMICAL PRODUCTS,
vinyl dispersions, for instance Mexomere PAM, aqueous dispersions of polyvinyl acetate, for instance Vinybran® from the company Nisshin Chemical or those sold by the company Union Carbide, aqueous dispersions of vinylpyrrolidone/dimethylaminopropylmethacrylamide/lauryldimethylpropylmethacrylamidoammonium chloride terpolymer, such as Styleze W® from ISP,
aqueous dispersions of polyurethane/polyacrylic hybrid polymers, such as those sold under the references Hybridur® by the company Air Products or Duromer® from National Starch,
dispersions of particles of core-shell type, such as those sold by the company Arkema under the reference Kynar® (core: fluoro-shell: acrylic) or else those described in U.S. Pat. No. 5,188,899 (core: silica-shell: silicone), and mixtures thereof.

According to one preferred embodiment, a composition in accordance with the invention comprises an aqueous dispersion of particles chosen from aqueous dispersions of acrylic film-forming polymer(s) and derivatives, in particular of styrene-acrylic and derivatives, and aqueous dispersions of polyurethane polymer(s), in particular of polyester-polyurethane, and derivatives thereof, and a mixture or mixtures thereof.

According to one advantageous embodiment, the total content of hard wax(es) and the total content of particles of film-forming polymer(s) are such that the weight ratio of the hard wax(es) to the particles of film-forming polymer(s) is greater than or equal to 1/2 and better still greater than or equal to 2/3. Preferably, this ratio is inclusively between 1/2 and 2, and even more preferentially between 2/3 and 3/2.

According to one advantageous embodiment, the total content of hard wax(es) and the total content of particles of film-forming polymer(s), both preferentially present in the form of particles in an aqueous dispersion, with the film-forming polymer(s) chosen from aqueous dispersions of acrylic film-forming polymer(s) and derivatives, in particular of styrene-acrylic and derivatives, and aqueous dispersions of polyester-polyurethane hybrid polymer(s), and mixture thereof, are such that the weight ratio of the particles of hard wax(es) to said particles of film-forming polymer(s) is greater than or equal to 1/2 and better still greater than or equal to 2/3.

Preferably, this ratio is inclusively between 1/2 and 2, and even more preferentially between 2/3 and 3/2.

Water-Soluble Film-Forming Polymer

The compositions according to the present invention comprise at least one water-soluble film-forming polymer.

Preferably, composition according to the invention is free of water-soluble film-forming polymer. However, the total dry matter content in terms of "water-soluble film-forming polymer(s)" can range from 0.1% to 10%, preferably from 0.5% to 8% and better still from 1% to 5% by weight, relative to the total weight of the composition.

Mention may be made, as examples of water-soluble film-forming polymers, of:
proteins, for instance proteins of vegetable origin, such as wheat or soybean proteins, or proteins of animal origin, such as keratins, for example keratin hydrolysates and sulfonic keratins;
cellulose polymers, such as hydroxyethylcellulose, hydroxypropylcellulose, methylcellulose, ethylhydroxyethylcellulose or carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

anionic, cationic, amphoteric or non-ionic chitin or chitosan polymers;

gums arabic, guar gum, xanthan derivatives, karaya gum or acacia gum;

alginates and carrageenans;

glycoaminoglycans, hyaluronic acid and its derivatives;

deoxyribonucleic acid;

mucopolysaccharides, such as chondroitin sulfates;

and mixtures thereof.

The total content of anionic associative polymer(s) and the total content of film-forming polymer(s) are such that the weight ratio of anionic associative polymer(s) to film-forming polymer(s) is greater than or equal to 1/150, preferably inclusively between 1/100 and 1/5, more preferentially between 1/60 and 1/10.

More particularly, the total content of anionic associative polymer(s) and the total content of film-forming polymer(s) as an aqueous dispersion are such that the weight ratio of anionic associative polymer(s) to film-forming polymer(s) as an aqueous dispersion is greater than or equal to 1/150, preferably inclusively between 1/100 and 1/5, more preferentially between 1/60 and 1/10.

Gelling Agents

Hydrophilic Gelling Agents

The compositions according to the present invention can also comprise at least one hydrophilic or water-soluble gelling agent and they can be chosen from:

copolymers of acrylic acid and of acrylamide sold in the form of their sodium salt under the names Reten® by the company Hercules and the sodium salts of polyhydroxycarboxylic acids sold under the name Hydagen F® by the company Henkel, AMPS (polyacrylamidomethylpropanesulfonic acid partially neutralized with aqueous ammonia and highly crosslinked), sold by the company Clariant, AMPS/acrylamide copolymers of SepiGel® or Simul-Gel® type sold by the company SEPPIC, and AMPS/polyoxyethylenated alkyl methacrylate copolymers (crosslinked or non-crosslinked), and mixtures thereof, associative polymers and in particular associative polyurethanes, such as the $C_{16}$-$OE_{120}$-$C_{16}$ polymer from the company Elementis (sold under the name Rheolate FX1100, which molecule has a urethane function and a weight-average molecular weight of 1300), OE being an oxyethylene unit, Rheolate 205, having a urea function, sold by the company Rheox, or also Rheolate 208 or 204 (these polymers being sold in pure form) or DW 1206B from Rohm & Haas, having a $C_{20}$ alkyl chain and having a urethane bond, sold at 20%, with respect to active material, in water. It is also possible to use solutions or dispersions of these associative polyurethanes, in particular in water or in aqueous/alcoholic medium. Mention may be made, as examples of such polymers, of Rheolate FX1010, Rheolate FX1035, Rheolate1070, Rheolate 255, Rheolate 278 and Rheolate 244, sold by the company Elementis. It is also possible to use the products DW 1206F and DW 1206J and also Acrysol RM 184 or Acrysol 44 from the company Rohm & Haas or also Borchigel LW 44 from the company Borchers, and mixtures thereof.

Some water-soluble film-forming polymers also act as a water-soluble gelling agent.

The hydrophilic gelling agents can be present in the compositions according to the invention at a content ranging from 0.05% to 10% by weight, relative to the total weight of the composition, preferably from 0.1% to 5% by weight and better still from 0.5% to 2% by weight.

A composition according to the invention advantageously comprises one of the above-mentioned gelling agents, preferably chosen from AMPS (polyacrylamidomethylpropanesulfonic acid partially neutralized with aqueous ammonia and highly crosslinked), AMPS/acrylamide copolymers, and a mixture thereof.

Lipophilic Gelling Agents

A composition according to the invention may comprise at least one lipophilic or liposoluble gelling agent.

The gelling agent(s) that may be used may be organic or mineral, polymeric or molecular lipophilic gelling agents.

As inorganic lipophilic gelling agents, mention may be made of clays, modified clays, such as Bentone 38 VCG from the company Elementis, and fumed silica optionally hydrophobically surface-treated.

The polymeric organic lipophilic gelling agents are, for example, partially or completely crosslinked elastomeric organopolysiloxanes of three-dimensional structure, for instance those sold under the names KSG6®, KSG16® and KSG18® by the company Shin-Etsu, Trefil E-505C® and Trefil E-506C® by the company Dow Corning, Gransil SR-CYC®, SR DMF10®, SR-DC556®, SR 5CYC Gel®, SR DMF 10 Gel® and SR DC 556 Gel® by the company Grant Industries and SF 1204® and JK 113® by the company General Electric; ethylcellulose, for instance the product sold under the name Ethocel® by the company Dow Chemical; polycondensates of polyamide type resulting from the condensation between (α) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or amidated with at least one saturated and linear monoalcohol or monoamine containing from 12 to 30 carbon atoms, and in particular ethylenediamine/stearyl dilinoleate copolymers such as the product sold under the name Uniclear 100 VG® by the company Arizona Chemical; silicone polyamides of the polyrganosiloxane type, such as those described in documents U.S. Pat. No. 5,874,069, U.S. Pat. No. 5,919,441, U.S. Pat. No. 6,051,216 and U.S. Pat. No. 5,981,680, for instance those sold under the reference Dow Corning 2-8179 and Dow Corning 2-8178 Gellant by the company Dow Corning. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name VersaGel®, for instance the mixture of butylene/ethylene/styrene triblock copolymer and of ethylene/propylene/styrene star copolymer in isododecane (Versagel M 5960).

The compositions according to the invention may also comprise a non-emulsifying silicone elastomer as lipophilic gelling agent. Among the lipophilic gelling agents that may also be mentioned are organogelling agents.

A composition according to the invention is preferably free of lipophilic gelling agent.

Colorants

The compositions in accordance with the invention comprise at least one colorant.

This (or these) colorant(s) is (are) preferably chosen from pulverulent colorants, fat-soluble dyes, water-soluble dyes and mixtures thereof.

Preferably, the compositions according to the invention comprise at least one pulverulent colorant. The pulverulent colorants can be chosen from pigments and pearlescent agents, preferably from pigments.

The pigments can be white or coloured, inorganic and/or organic and coated or uncoated. Mention may be made, among the inorganic pigments, of metal oxides, in particular titanium dioxide, optionally surface-treated, zirconium, zinc or cerium oxide, and also iron, titanium or chromium oxide, manganese violet, ultramarine blue, chromium hydrate and ferric blue. Mention may be made, among the organic pigments, of carbon black, pigments of D & C type and lakes based on cochineal carmine of barium, strontium, calcium or aluminium.

The pearlescent agents can be chosen from white pearlescent pigments, such as mica covered with titanium dioxide or with bismuth oxychloride, coloured pearlescent pigments, such as titanium oxide-coated mica with iron oxides, titanium oxide-coated mica with in particular ferric blue or chromium oxide, or titanium oxide-coated mica with an organic pigment of the abovementioned type, and also pearlescent pigments based on bismuth oxychloride.

The fat-soluble dyes are, for example, Sudan red, D&C Red 17, D&C Green 6, β-carotene, soybean oil, Sudan brown, D&C Yellow 11, D&C Violet 2, D&C Orange 5, quinoline yellow and annatto.

Preferably, the pigments present in the compositions according to the invention are chosen from metal oxides.

These colorants can be present at a content ranging from 0.01% to 30% by weight, relative to the total weight of the composition, in particular from 3% to 22% by weight, relative to the total weight of the composition.

Preferably, the colorant(s) is (are) chosen from one or more metal oxides present at a content greater than or equal to 2% by weight, relative to the total weight of the composition, advantageously inclusively between 3% and 22% by weight, relative to the total weight of the composition.

Fillers

The compositions in accordance with the invention may also comprise at least one filler.

The fillers may be chosen from those that are well known to those skilled in the art and commonly used in cosmetic compositions. The fillers may be inorganic or organic, and lamellar or spherical. Mention may be made of mica, talc, silica, kaolin, polyamide powders, for instance the Nylon® sold under the name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids having from 8 to 22 carbon atoms and in particular from 12 to 18 carbon atoms, for example zinc, magnesium or lithium stearate, zinc laurate and magnesium myristate.

The fillers may represent from 0.1% to 15% by weight and in particular from 0.5% to 10% by weight relative to the total weight of the composition.

Cosmetic Active Agents

The compositions in accordance with the invention may also comprise at least one cosmetic active agent.

Mention may in particular be made, as cosmetic active agents which can be used in the compositions in accordance with the invention, of antioxidants, preservatives, fragrances, neutralizing agents, emollients, coalescence agents, moisturizing agents, vitamins and screening agents, in particular sunscreens, and mixtures thereof.

Needless to say, those skilled in the art will take care to select the optional additional additives and/or the amount thereof such that the advantageous properties of the composition according to the invention are not, or are not substantially, adversely affected by the envisaged addition.

Preferably, the composition according to the invention is a leave-in composition. Advantageously, the composition is a makeup composition and in particular a mascara.

Oil or Organic Solvent

The compositions according to the invention can comprise at least one oil or organic solvent.

The compositions according to the invention can in particular comprise at least one oil chosen from at least one non-volatile oil, at least one volatile oil, and a mixture thereof.

Non-Volatile Oil

The term "oil" is understood to mean a fatty substance which is liquid at ambient temperature and atmospheric pressure.

The term "non-volatile oil" is understood to mean an oil which remains on the skin or the keratin fibre at ambient temperature and pressure. More specifically, a non-volatile oil exhibits an evaporation rate of strictly less than 0.01 mg/cm$^2$/min.

In order to measure this evaporation rate, 15 g of oil or of oil mixture to be tested are introduced into a crystallizing dish with a diameter of 7 cm placed on a balance in a large chamber of approximately 0.3 m$^3$ which is regulated in temperature, at a temperature of 25° C., and regulated in hygrometry, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The weight of oil remaining in the crystallizing dish is measured at regular intervals. The evaporation rates are expressed in mg of oil evaporated per unit of surface area (cm$^2$) and per unit of time (minute).

Said at least one non-volatile oil can be chosen from hydrocarbon-based oils and silicone oils, and mixtures thereof, preferably from hydrocarbon-based oils.

The non-volatile hydrocarbon-based oils suitable for the present invention can be chosen in particular from:
hydrocarbon-based oils of vegetable origin, such as triglycerides composed of esters of fatty acids and of glycerol, the fatty acids of which can have varied chain lengths from $C_4$ to $C_{28}$, it being possible for the latter to be linear or branched and saturated or unsaturated; these oils are in particular wheat germ oil, sunflower oil, grape seed oil, sesame oil, maize oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkinseed oil, cucumber oil, blackcurrant oil, evening primrose oil, millet oil, barley oil, quinoa oil, rye oil, safflower oil, candlenut oil, passionflower oil and musk rose oil; or alternatively caprylic/capric acid triglycerides, such as those sold by the company Stéarineries Dubois or those sold under the names Miglyol 810®, 812® and 818® by the company Sasol;

synthetic ethers having from 10 to 40 carbon atoms;

linear or branched hydrocarbons of mineral or synthetic origin, other than the polymers according to the invention, such as petrolatum, polybutenes, polydecenes, squalane and mixtures thereof;

synthetic esters, such as oils of formula $R_1COOR_2$ in which $R_1$ represents the residue of a linear or branched fatty acid comprising from 1 to 40 carbon atoms and $R_2$ represents a hydrocarbon-based chain, in particular a branched hydrocarbon-based chain, comprising from 1 to 40 carbon atoms, provided that $R_1+R_2>10$, such as, for example, purcellin oil (cetearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, or octanoates, decanoates or ricinoleates of alcohols or polyalcohols, such as propylene glycol dioctanoate; hydroxylated esters, such as isostearyl lactate or diisostearyl malate; and pentaerythritol esters;

fatty alcohols which are liquid at ambient temperature and which comprise a branched and/or unsaturated carbon-based chain having from 12 to 26 carbon atoms, such as octyldodecanol, isostearyl alcohol, oleyl alcohol, 2-hexyldecanol, 2-butyloctanol or 2-undecylpentadecanol;

higher fatty acids, such as oleic acid, linoleic acid, linolenic acid and mixtures thereof.

The non-volatile silicone oils suitable for the present invention can be chosen in particular from:

the non-volatile silicone oils that may be used in the composition in accordance with the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

A composition according to the invention optionally comprises at least one non-volatile hydrocarbon-based oil of vegetable origin, such as triglycerides consisting of esters of fatty acids and of glycerol, the fatty acids of which can have varied chain lengths from $C_4$ to $C_{28}$, in particular palm oil and hydrogenated jojoba oil. A composition according to the invention is preferably devoid of non-volatile silicone oil(s).

A composition according to the invention is preferably devoid of non-volatile oil. However, the total content of non-volatile oil(s) in a composition in accordance with the invention can range from 0.01% to 10% by weight, in particular from 0.1% to 8% by weight and preferably from 0.25% to 5% by weight, relative to the total weight of the composition.

According to a preferred embodiment, a composition according to the invention comprises less than 5% by weight of non-volatile oil(s), relative to the total weight of the composition.

Volatile Oil

The composition according to the invention may comprise at least one volatile oil.

The term "volatile oil" is understood to mean an oil (or non-aqueous medium) capable of evaporating on contact with the skin in less than one hour, at ambient temperature and atmospheric pressure. The volatile oil is a volatile cosmetic oil which is liquid at ambient temperature. More specifically, a volatile oil exhibits an evaporation rate of between 0.01 and 200 mg/cm²/min, limits included.

This volatile oil can be a hydrocarbon-based oil.

The volatile hydrocarbon-based oil can be chosen from hydrocarbon-based oils having from 7 to 16 carbon atoms.

The composition according to the invention can comprise one or more volatile branched alkane(s). The term "one or more volatile branched alkane(s)" is understood to mean, without distinction, "one or more volatile branched alkane oil(s)".

Mention may in particular be made, as volatile hydrocarbon-based oil having from 7 to 16 carbon atoms, of branched $C_8$-$C_{16}$ alkanes, such as $C_8$-$C_{16}$ isoalkanes (also known as isoparaffins), isododecane, isodecane, isohexadecane, for example the oils sold under the Isopar or Permethyl trade names, branched $C_8$-$C_{16}$ esters, such as isohexyl neopentanoate, and mixtures thereof. Preferably, the volatile hydrocarbon-based oil having from 8 to 16 carbon atoms is chosen from isododecane, isodecane, isohexadecane and mixtures thereof, and is in particular isododecane.

The composition according to the invention can comprise one or more volatile linear alkane(s). The term "one or more volatile linear alkane(s)" is understood to mean, without distinction, "one or more volatile linear alkane oil(s)".

A volatile linear alkane which is suitable for the invention is liquid at ambient temperature (approximately 25° C.) and at atmospheric pressure (760 mmHg).

A "volatile linear alkane" which is suitable for the invention is understood to mean a cosmetic linear alkane which is capable of evaporating on contact with the skin in less than one hour at ambient temperature (25° C.) and atmospheric pressure (760 mmHg, that is to say 101 325 Pa) and which is liquid at ambient temperature, having in particular an evaporation rate ranging from 0.01 to 15 mg/cm²/min at ambient temperature (25° C.) and atmospheric pressure (760 mmHg).

The linear alkanes, preferably of vegetable origin, comprise from 7 to 15 carbon atoms, in particular from 9 to 14 carbon atoms and more particularly from 11 to 13 carbon atoms.

Mention may be made, as example of linear alkane suitable for the invention, of the alkanes described in patent applications WO 2007/068371 or WO 2008/155059 from Cognis (mixtures of distinct alkanes which differ by at least one carbon). These alkanes are obtained from fatty alcohols, themselves obtained from coconut oil or palm oil.

Mention may be made, as example of linear alkane suitable for the invention, of n-heptane ($C_7$), n-octane ($C_9$), n-nonane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$) and mixtures thereof, in particular the mixture of n-undecane ($C_{11}$) and n-tridecane ($C_{13}$) described in Example 1 of application WO 2008/155059 of Cognis. Mention may also be made of n-dodecane ($C_{12}$) and n-tetradecane ($C_{14}$), sold by Sasol respectively under the references Parafol 12-97 and Parafol 14-97, and also mixtures thereof.

Use may be made of the linear alkane alone or as a mixture of at least two distinct alkanes which differ from one another by a carbon number of at least 1, in particular a mixture of at least two distinct linear alkanes comprising from 10 to 14 carbon atoms which differ from each other by a carbon number of at least 2, in particular a mixture of volatile linear $C_{11}/C_{13}$ alkanes or a mixture of linear $C_{12}/C_{14}$ alkanes, in particular an n-undecane/n-tridecane mixture (such a mixture can be obtained according to Example 1 or Example 2 of WO 2008/155059).

In an alternative form or additionally, the composition prepared can comprise at least one volatile silicone oil or solvent which is compatible with a cosmetic use.

The term "silicone oil" is understood to mean an oil containing at least one silicon atom, and in particular containing Si-O groups. According to one embodiment, said composition comprises less than 10% by weight of non-volatile silicone oil(s), relative to the total weight of the composition, better still less than 5% by weight, or even is free of silicone oil.

Volatile silicone oils that may be mentioned include cyclic polysiloxanes and linear polysiloxanes, and mixtures thereof. Volatile linear polysiloxanes that may be mentioned include hexamethyldisiloxane, octamethyltrisiloxane, decamethyltetrasiloxane, tetradecamethylhexasiloxane and hexadecamethylheptasiloxane. Volatile cyclic polysiloxanes that may be mentioned include hexamethylcyclotrisiloxane, octamethylcyclotetrasiloxane, decamethylcyclopentasiloxane and dodecamethylcyclohexasiloxane.

As a variant or additionally, the composition prepared may comprise at least one volatile fluoro oil.

The term "fluoro oil" is understood to mean an oil containing at least one fluorine atom.

Mention may be made, as volatile fluoro oil, of nonafluoromethoxybutane or perfluoromethylcyclopentane, and mixtures thereof.

A composition according to the invention is preferably free of non-volatile oil. However, at least one volatile oil may be present at a total content ranging from 0.1% to 10% by weight. In particular, the volatile oil can be present in the composition at a content ranging from 0.5% to 5% by weight, relative to the total weight of the composition.

According to a preferred embodiment, a composition according to the invention comprises less than 5% by weight of volatile oil(s), relative to the total weight of the composition.

Assembly

An assembly for coating keratin fibres suitable for the invention can comprise an applicator configured in order to apply said cosmetic composition for coating keratin fibres and, where appropriate, a packaging device suitable for receiving said composition. According to one particular embodiment, such an assembly may comprise means for heating a composition in accordance with the invention.

Heating Means

A composition in accordance with the invention can be subjected to heating means before and/or during application.

These heating means can be rigidly connected to an assembly for coating keratin fibres and more particularly to an applicator configured in order to apply said cosmetic composition for coating keratin fibres and, where appropriate, a packaging device suitable for receiving said composition.

These heating means are then suitable for melting at least one part of the fatty phase, and in particular at least one part of the emulsifying system and, where appropriate, at least one part of the soft wax(es) and, optionally at least one part of the particles of hard wax(es). The wax particles are heated at a temperature $T_c$ such that only a part of the crystallized chains is melted.

The heating means can also come into contact with or come to be opposite the composition to be heated.

The composition can be heated while it is contained in a packaging device.

The composition can be heated while it is at least partially exposed to ambient air.

The composition can be heated locally at a temperature greater than or equal to 45° C., or even greater than or equal to 50° C., or else greater than or equal to 55° C. The temperature of the composition must not cause any risk of burning at the moment of application. This is why, when the composition is heated before application, a waiting time between the moment at which the composition is heated and the application to the keratin materials may optionally be necessary.

According to one embodiment variant, the composition is heated simultaneously with its application to the keratin fibres.

According to another variant, the composition is heated before and during its application to the keratin fibres.

The temperature at which at least one part of the composition is heated may be inclusively between 45° C. and 95° C., better still 50° to 85° C. and even better still 55° C. to 75° C.

The temperature may, for example, be measured at the surface using an infrared pyrometer, for example of the Fluke® brand.

The composition in accordance with the invention is capable of reversibly changing from a solid state to an at least partially liquid, or even totally liquid, state.

The solid/liquid change of state is at least partly due to the melting of a crystalline part, in particular of the wax(es) described above in this description.

The total enthalpy of fusion of the composition is the enthalpy consumed by the composition between −20° C. and 120° C. The total enthalpy of fusion of the composition is equal to the area under the curve of the thermogram obtained using a differential scanning calorimeter (DSC), such as the calorimeter sold under the name MDSC 2920 by TA Instruments, with a temperature rise of 5° C. or 10° C. per minute, according to Standard ISO 11357-3:1999.

Measurement Protocol:

A sample of 5 mg of composition is placed in a crucible and subjected to a first temperature rise which goes from −20° C. to 120° C., at a heating speed of 10° C./minute, and then is cooled from 120° C. à−20° C. at a cooling speed of 10° C./minute. The sample is kept at −20° C. for 5 min and, finally, subjected to a second temperature rise which goes from −20° C. to 100° C., at a heating speed of 5° C./minute.

During the second temperature rise, the variation in the difference in power absorbed by an empty crucible and by the crucible containing the sample of the composition is measured as a function of the temperature. The melting point of the compound is the value of the temperature corresponding to the tip of the peak of the curve representing the variation in the difference in power absorbed as a function of the temperature.

The enthalpy of fusion of the composition consumed at the temperature $T_c$ is the amount of energy required to make the compound pass from the solid or very viscous state at −20° C. to the state of the composition at the temperature $T_c$. It is expressed in J/g.

According to one embodiment of the invention, the composition is chosen such that the ratio of the enthalpy consumed between −20° C. and $T_c$ by the product to the total enthalpy consumed between −20° C. and 120° C. is less than or equal to 0.7.

This relationship is, for example, confirmed for a temperature $T_c$ of the composition of between 45° C. and 80° C.

The choice of the temperature $T_c$ to which the composition is brought by the heating means may thus be made in such a way that said ratio is less than or equal to 0.7, for example inclusively between 0.3 and 0.6. In other words, heating is carried out to a temperature such that the ratio of the enthalpy supplied in order to heat the sample of composition to the temperature $T_c$ to the total enthalpy is less than or equal to 0.7, such a parameter being measured according to the DSC protocol described above.

Only the heated composition can come into contact with the keratin fibres, for example the eyelashes, during the application.

Applicator

The applicator can comprise means which make it possible to smooth and/or separate keratin fibres, such as the eyelashes or eyebrows, in particular in the form of teeth, bristles or other protruding parts.

The applicator is designed in order to apply the composition to the eyelashes or eyebrows and can comprise, for example, a brush or a comb.

The applicator can also be used for finishing the makeup, over a region of the eyelashes or eyebrows which is made up or laden with the composition.

The brush can comprise a twisted core and bristles held between the turns of the core or can be made in yet another way.

The comb is, for example, produced from a single part by moulding plastic.

In some implementational examples, the application element is mounted at the end of a stem which can be flexible, which can contribute to improving the comfort during application.

Packaging Device

The packaging device can comprise a container intended to house the composition for coating keratin fibres. This composition can then be withdrawn from the container by immersing the applicator in it.

This applicator can be integral with an element for closing the container. This closing element can form a member for grasping the applicator. This grasping member can form a cap to be removably mounted on said container by any suitable means, such as screwing, snap-fastening, push-fitting or other. Such a container can thus reversibly house said applicator.

This container can optionally be equipped with a wiper suitable for removing a surplus of product withdrawn by the applicator.

A method for applying the composition according to the invention to the eyelashes or eyebrows can also comprise the following steps:
forming a deposited layer of the cosmetic composition on the eyelashes or eyebrows,
leaving the deposited layer on the eyelashes or eyebrows, it being possible for the deposited layer to dry.

It should be noted that, according to another embodiment, the applicator can form a product container. In such a case, a container can, for example, be provided in the grasping member and an internal channel can internally connect this grasping member to the protruding application elements.

Finally, it should be noted that the packaging and application assembly can be provided in the form of a kit, it being possible for the applicator and the packaging device to be housed separately in one and the same packaging article.

The previous and following examples are given by way of illustration of the present invention, and cannot limit the scope thereof.

EXAMPLE

A mascara composition in accordance with the invention and a comparative mascara composition outside the invention have been described below:

|  | Ingredients with percentage contents | Comparative composition outside the invention | Composition according to the invention |
|---|---|---|---|
| Phase A | Carnauba wax SP 63 from Strahl & Pitsch | 26 | 26 |
|  | Anionic associative polymer as an aqueous dispersion at 30% (Aculyn 22 from Rohm and Haas (Dow Chemical)) | 0 | 0.9 |
|  | Hydroxyethylcellulose | 0.5 | 0 |
|  | Oxyethylenated glyceryl monostearate (30 OE) (Tagat S from Evonik Goldschmidt) | 7.50 | 7.50 |
|  | Water | 24 | 23.4 |
|  | Pigments | 7 | 7 |
| Phase B | Acrylic and styrene/acrylic copolymers as an aqueous 40% emulsion in a water/butylene glycol/protected sodium lauryl ether sulfate mixture (Syntran 5760 CG from Interpolymer) | 35 | 35 |
| Phase C | Water | 0 | 0.1 |
|  | 50% potassium hydroxide | 0 | 0.1 |

These compositions were prepared as follows:

i. Preparation of Phase A

All the starting materials used are carefully weighed out using a balance (accuracy 0.01 g). The various waxes are melted in a 500 ml jacketed heating pan with circulation of hot oil to control the temperature. Heating is carried out at approximately 95-98° C. Once the waxes have melted, homogenization is carried out by stirring using a Moritz stirrer, which is a stirrer of rotor-stator type. It is composed of a stationary part within which a second mobile part rotates at variable speed; this device is used to prepare emulsions since it makes possible very high shearing.

When the waxes are molten and homogenized, the anionic associative polymer, or the hydroxyethylcellulose according to the comparative example outside the invention (in excess), the oxyethylenated glyceryl monostearate, the water and the pigments are then added, and the mixture is emulsified for 10 minutes.

ii. Preparation of Phase B

Phase B is placed in a jacketed heating vessel thermostated at 5° C. with stirring with a Rayneri mixer.

iii. Mixing Phase B with Phase A

The hot emulsion (phase A at 95° C.) is then poured into phase B with stirring.

iv. Addition of Phase C to Preparation A+B

The potassium hydroxide is then diluted in water and the diluted potassium hydroxide is poured into the mixture of phase B and phase A (only for the composition according to the invention in order to neutralize the anionic associative polymer).

v. End of Formulation

The mascara thus obtained is transferred into a closed jar in order to prevent it from drying on contact with the air; it is then necessary to wait 24 hours in order to confirm that the formulation is homogenous and that the pigments are correctly dispersed.

It should be noted that other mascara formulae can be prepared while taking the following preparation elements into consideration. In particular, it is recommended:

in a first phase, to incorporate into the compounds to be subjected to heating the thickening compounds (wax(es) and anionic associative polymer(s), where appropriate, compounds chosen, for example, from gelling agents, film-forming polymers which are in particular water soluble, fillers, pasty fatty substances, etc), the water, one or more emulsifying system(s), it being given that the water content used is greater than 25% by weight relative to the total weight of this first phase, preferably greater than 30% by weight, or even greater than 35% by weight, relative to the total weight of this first phase, and that the total content of hard wax(es), and optionally of additional wax(es), and the total content of emulsifying system(s) are such that the weight ratio of the wax(es) plus the additional wax(es)/the emulsifying system(s) is inclusively between 2 and 6, more preferentially between 3 and 5, and the colorant(s), in the knowledge that the order of addition of the compounds is unimportant, it being understood that it is, however, preferable for the water not to be present at first, in order to avoid any early evaporation; the whole mixture is emulsified with stirring at a temperature above the melting point of the wax(es) having the maximum melting point, in a second phase, to place an aqueous phase optionally comprising, or optionally being formed by, an aqueous dispersion of particles of film-forming polymers in a vessel in which the temperature is regulated inclusively between 0 and 45° C. (although a temperature of 5° C. is previously exemplified, it is understood that any temperature inclusively between 0 and 45° C., more preferentially inclusively between 0 and 20° C. will result in a composition prepared in accordance with the method according to the invention), the order of preparation of the first phase and of the second phase being unimportant, to pour the first phase, at a temperature above the maximum melting point of the wax(es), into the vessel at a temperature regulated between 0 and 45° C., and preferably between 0 and 20° C., containing the second phase, to leave to stir until the temperature of the mixture stabilizes at the regulated temperature;

when a preserving system is used, it may be advantageous to add this preserving system once the mixing of the first phase and the second phase has been carried out, and preferentially once the mixture drops in temperature, advantageously once the mixture reaches the regulated temperature of between 0 and 45° C., and preferably between 0 and 20° C., preferentially, adding a base, such as KOH, able to neutralize the associative polymer.

It is important to note that some compounds which are part of this "first phase" can be prepared independently, but subsequently integrated while hot with the wax(es). For example, the pigment(s) may be prepared separately from the wax(es), but are subsequently added with the wax(es) while hot ("while hot" meaning a temperature above or equal to the melting point of the wax(es) enabling all the waxes to be in the molten state). Thus, this "first phase" comprises all the compounds which, from the beginning, or during a successive step, undergo an emulsification operation while hot with the wax(es), prior to the mixing with the aqueous phase while cold, and optionally with the aqueous dispersion of film-forming polymer(s) while cold ("while cold" meaning that the aqueous phase or the aqueous dispersion is at a temperature, which is optionally regulated, between 0 and 45° C.).

This preparation protocol makes it possible, surprisingly and unexpectedly, to obtain, in particular in the presence of a high solids content, for example greater than 45%, compounds which have a smooth, glossy appearance, which have an intense colour and are easy and comfortable to apply, but which nevertheless have the desired volume effect by virtue of the incorporation of a high content of wax(es), and good water resistance by virtue of the presence of a high content of particles of film-forming polymer(s).

It should be noted that a composition prepared by means of the production method as described has distinct and advantageous structural and functional characteristics in comparison with a conventional production method consisting in preparing a first phase of wax(es) which is molten at 95° C., adding the water, heated beforehand to 90-92° C., to the waxes at 95° C., then allowing it to cool, generally in the open air, to ambient temperature. Indeed, in the method according to the invention, the phase containing in particular the waxes is abruptly immersed in a cold aqueous phase, conferring advantageous properties of wax dispersion and of cosmeticity. Thus, using according to the present invention the aqueous dispersion of the film-forming polymer(s) for emulsifying the hard wax(es) is unexpected.

2/ Protocols and Results

The compositions prepared are observed with the naked eye and under a microscope, and then tested on a test sample of unsullied eyelashes, by application of these compositions using a brush.

The comparative composition outside the invention employing hydroxyethylcellulose as thickening polymer, even used in excess with respect to the composition according to the invention, is too fluid, making it unusable as makeup, the latter having a viscosity at 25° C. of 1.8 Pa·s measured by the Rheomat RM100® instrument.

The composition according to the invention exhibits to the naked eye and under a microscope a fine emulsion with a fine and well-distributed (homogeneous) grain of wax(es). The compositions in accordance with the invention are pleasant to apply, they have a fluid texture (viscosity at 25° C. of 7.1 Pa·s measured using the Rheomat RM100® instrument), the deposit is constructed layer upon layer, the composition coats the eyelashes well, the makeup result is even, and the eyelash fringe is well developed. Furthermore, the composition obtained is nice and glossy. Moreover, the pigments are well dispersed, and the composition is intensely black. In addition, these compositions are stable at 4 and 45° C. for two months.

It should be noted that the protocols for measuring the gloss and the intensity of the black that are to be carried out in the context of the present invention are described in patent application FR 2 968 978, page 44, lines 1 to 21.

It is understood that, in the context of the present invention, the weight percentages given for a compound or a family of compounds are always expressed as weight of dry matter of the compound in question.

Throughout the application, the wording "comprising a" means "comprising at least one", unless otherwise specified.

The invention claimed is:

1. A cosmetic composition, comprising:
   an aqueous phase comprising at least one film-forming polymer;
   a fatty phase, wherein the fatty phase is dispersed in the aqueous phase and the fatty phase comprises particles comprising a hard wax having a melting point ranging from 65° C. to 120° C.; and
   greater than or equal to 3% by weight relative to the total weight of the composition of at least one non-ionic surfactant with an HLB value at 25° C. greater than or equal to 8 selected from the group consisting of:
      oxyalkylenated glycerol ethers,
      oxyalkylenated alcohols,
      fatty acid esters of polyethylene glycol,
      oxyalkylenated esters of fatty acids and of glycerol ethers,
      oxyalkylenated esters of fatty acids and of sorbitol ethers and mixture(s) thereof; and
   from 0.1% to 1% by weight of at least one anionic associative polymer relative to a total weight of the composition;
   wherein
   the composition is a wax-in-water emulsion,
   wherein the composition is in the form of a mascara,
   the composition comprises a solids content greater than or equal to 42% by weight relative to the total weight of the composition,
   a viscosity of the composition at 25° C. is from 5 to 50 Pa·s;
   a content of the hard wax is at least 10% by weight relative to the total weight of the composition;
   the anionic associative polymer comprises:
      at least one backbone chain derived from a monomer of (meth)acrylic acid, ester(s) thereof, salt(s) thereof, and/or mixtures thereof,
      at least one hydrophobic chain comprising a linear and saturated $C_8$-$C_{24}$ chain, and
      at least one alkoxylated or glycerolated spacer linking the backbone chain and the hydrophobic chain, and
      a weight ratio of the anionic associative polymer to the non-ionic surfactant with an HLB value at 25° C. greater than or equal to 8 is from 1/60 to 1/2.

2. The composition according to claim 1, wherein the hard wax is polar.

3. The composition according to claim 1, wherein the hydrophobic chain and the alkoxylated or glycerolated spacer extend, in continuity, with respect to one another, laterally relative to the backbone chain.

4. The composition according to claim 1, wherein the anionic associative polymer is selected from the group consisting of Acrylates/Steareth-20 Methacrylate Copolymer, Acrylates/Beheneth-25 Methacrylate Copolymer, and a mixture thereof.

5. The composition according to claim 1, wherein the aqueous phase is from 30% to 80% by weight, relative to the total weight of the composition.

6. The composition according to claim 1, wherein the particles of the hard wax are not introduced into the preparation of the composition in the form of a prepared aqueous microdispersion of the hard wax.

7. The composition according to claim 1, wherein the film forming polymer is at least one aqueous dispersion of particles, the film-forming polymer being present at a dry matter content greater than or equal to 5% by weight relative to the total weight of the composition.

8. The composition according to claim 7, wherein the particles of film-forming polymer are introduced into the preparation of the composition in the form of a prepared aqueous dispersion of the film-forming polymer.

9. The composition according to claim 1, wherein a total content of the particles of the hard wax is greater than or equal to 12% by weight, relative to the total weight of the composition.

10. The composition according to claim 1, wherein a total content of the particles of the hard wax is at least 80% by weight, relative to the total weight of waxes.

11. The composition according to claim 1, wherein the non-ionic surfactant with an HLB value at 25° C. greater than or equal to 8, is selected from the group consisting of:
    oxyalkylenated glycerol ethers,
    oxyalkylenated alcohols,
    fatty acid esters of polyethylene glycol,
    and mixture(s) thereof.

12. The composition according to claim 1, further comprising a pulverulent colorant.

13. A method for coating keratin fibres, comprising applying the cosmetic composition according to claim 1 to keratin fibres.

14. A method for preparing the cosmetic composition of claim 1, comprising:
    in a first phase,
      heating the hard wax and optionally the additional wax, at a temperature above its melting point in order to melt the wax,
      adding the anionic associative polymer, an emulsifying system capable of dispersing at least the hard wax comprising a non-ionic surfactant with an HLB value at 25° C. greater than or equal to 8, and water, wherein a water content is greater than 25% by weight relative to the total weight of the first phase, and the total content of hard wax, and optionally of the additional wax, and the total content of emulsifying system are such that the weight ratio of the wax plus additional wax/emulsifying system is inclusively between 2 and 6,
      adding the colorants,
      optionally adding any other compound of thickening nature, or water-soluble film-forming polymers, wherein the water is not present in the beginning of the first phase in order to avoid any early evaporation, and
      emulsifying the whole mixture with stirring at a temperature above the melting point of the wax;
    in a second phase,
      placing an aqueous phase in a vessel in which the temperature is inclusively between 0 and 45° C. and the order in which the first phase and the second phase are prepared being of no importance;
    bringing the first and second phases together by pouring the first phase, still at a temperature above the melting point of the wax, into the vessel comprising the second phase having a temperature between 0 and 45° C.;
    leaving to stir until the temperature of the mixture stabilizes at the temperature between 0 and 45° C.;
    optionally adding a preserving system, once the temperature of the mixture of the first phase with the second phase has stabilized at the temperature of inclusively between 0 and 45° C.; and
    optionally adding a base able to neutralize the anionic associative polymer.

15. A cosmetic composition, comprising:
an aqueous phase comprising at least one film-forming polymer;
a fatty phase, wherein the fatty phase is dispersed in the aqueous phase and the fatty phase comprises particles comprising a hard wax having a melting point ranging from 65° C. to 120° C.;
greater than or equal to 3% by weight relative to the total weight of the composition of at least one non-ionic surfactant with an HLB value at 25° C. greater than or equal to 8 selected from the group consisting of:
oxyalkylenated glycerol ethers,
oxyalkylenated alcohols,
fatty acid esters of polyethylene glycol
oxyalkylenated esters of fatty acids and of glycerol ethers,
oxyalkylenated esters of fatty acids and of sorbitol ethers,
and mixture(s) thereof; and
from 0.1% to 1% by weight of at least one anionic associative polymer relative to a total weight of the composition; and
at least one base to neutralize the anionic associative polymer;
wherein
the composition is a wax-in-water emulsion,
the composition is in the form of a mascara,
the composition comprises a solids content greater than or equal to 42% by weight relative to the total weight of the composition,
a viscosity of the composition at 25° C. is from 5 to 50 Pa·s;
a content of the hard wax is at least 10% by weight relative to the total weight of the composition;
the anionic associative polymer comprises:
at least one backbone chain derived from a monomer of (meth)acrylic acid, ester(s) thereof, salt(s) thereof, and/or mixtures thereof,
at least one hydrophobic chain comprising a linear and saturated $C_8$-$C_{24}$ chain, and
at least one alkoxylated or glycerolated spacer linking the backbone chain and the hydrophobic chain, and
a weight ratio of the anionic associative polymer to the non-ionic surfactant with an HLB value at 25° C. greater than or equal to 8 is from 1/60 to 1/2.

16. The composition according to claim 15, wherein the base is potassium hydroxide.

17. The composition according to claim 1, wherein the weight ratio of the anionic associative polymer to the non-ionic surfactant with an HLB value at 25° C. greater than or equal to 8 is from 1/50 to 1/2.

18. The composition according to claim 1, wherein the weight ratio of the anionic associative polymer to the non-ionic surfactant with an HLB value at 25° C. greater than or equal to 8 is from 1/40 to 1/3.

19. The composition according to claim 1, wherein the non-ionic surfactant with an HLB value at 25° C. greater than or equal to 8, is selected from the group consisting of:
oxyalkylenated glycerol ethers,
fatty acid esters of polyethylene glycol,
oxyalkylenated esters of fatty acids and of glycerol ethers,
and mixture(s) thereof.

20. The composition according to claim 1, wherein the non-ionic surfactant with an HLB value at 25° C. greater than or equal to 8, is selected from the group consisting of:
oxyalkylenated glycerol ethers,
oxyalkylenated alcohols,
oxyalkylenated esters of fatty acids and of glycerol ethers,
and mixture(s) thereof.

* * * * *